(12) United States Patent
Protzer et al.

(10) Patent No.: US 10,711,054 B2
(45) Date of Patent: Jul. 14, 2020

(54) TRISPECIFIC BINDING MOLECULES FOR TREATING HBV INFECTION AND ASSOCIATED CONDITIONS

(71) Applicants: Helmholtz Zentrum München—Deutsches Forschungszentrum für Gesundheit und Umwelt (GmbH), Neuherberg (DE); DEUTSCHES KREBSFORSCHUNGSZENTRUM, Heidelberg (DE); TECHNISCHE UNIVERSITÄT MÜNCHEN, Munich (DE)

(72) Inventors: Ulrike Protzer, Munich (DE); Felix Bohne, Munich (DE); Oliver Quitt, Munich (DE); Frank Momburg, Heidelberg (DE); Gerhard Moldenhauer, Bad Arolsen (DE)

(73) Assignees: Helmholtz Zentrum München—Deutsches Forschungszentrum fur Gesundheit und umwelt (GmbH), Neuherberg (DE); DEUTSCHES KREBSFORSCHUNGSZENTRUM, Heidelberg (DE); TECHNISCHE UNIVERSITÄT MÜNCHEN, München (DE)

( * ) Notice: Subject to any disclaimer, the term of this patent is extended or adjusted under 35 U.S.C. 154(b) by 0 days.

(21) Appl. No.: 15/558,834

(22) PCT Filed: Mar. 16, 2016

(86) PCT No.: PCT/EP2016/055717
§ 371 (c)(1),
(2) Date: Sep. 15, 2017

(87) PCT Pub. No.: WO2016/146702
PCT Pub. Date: Sep. 22, 2016

(65) Prior Publication Data
US 2018/0079798 A1 Mar. 22, 2018

(30) Foreign Application Priority Data

Mar. 16, 2015 (EP) ..................... 15159274

(51) Int. Cl.
*C07K 16/08* (2006.01)
*C07K 16/28* (2006.01)
(Continued)

(52) U.S. Cl.
CPC .......... *C07K 16/082* (2013.01); *C07K 16/283* (2013.01); *C07K 16/2803* (2013.01);
(Continued)

(58) Field of Classification Search
None
See application file for complete search history.

(56) References Cited

U.S. PATENT DOCUMENTS

| 7,183,076 B2 * | 2/2007 | Arathoon ............... C07K 16/00 435/328 |
| 2009/0117108 A1 | 5/2009 | Wang et al. |
| 2014/0286999 A1 * | 9/2014 | Lindhofer ............ C07K 16/283 424/400 |

FOREIGN PATENT DOCUMENTS

| EP | 1378520 A1 | 1/2004 |
| EP | 1736484 A1 | 12/2006 |

(Continued)

OTHER PUBLICATIONS

Willems et al. (Cancer Immunology, 2005, p. 1059-1071).*
(Continued)

*Primary Examiner* — Agnieszka Boesen
(74) *Attorney, Agent, or Firm* — Pillsbury Winthrop Shaw Pittmann LLP

(57) ABSTRACT

The present invention relates to a binding molecule comprising at least three binding specificities, wherein (a) the first specificity is for a Hepatitis B virus (HBV) surface
(Continued)

antigen selected from HBV small surface antigen, HBV medium surface antigen and HBV large surface antigen; (b) (i) the second and third specificity are for CD3 and CD28, respectively; or (ii) the second and third specificity are selected from specificities for CD16, CD56, NKp30, NKp46, 4-1BB and NKG2D; and (c) each binding specificity is provided by one or more binding sites, each binding site being independently provided by (i) a set of six complementarity determining regions (CDRs), wherein said set of six CDRs consists of a first set of three CDRs and a second set of three CDRs, wherein said first and said second set is each comprised in an immunoglobulin domain; or (ii) a set of three CDRs, wherein said set of three CDRs is comprised in an immunoglobulin domain.

15 Claims, 10 Drawing Sheets

Specification includes a Sequence Listing.

(51) Int. Cl.
  *C07K 16/46* (2006.01)
  *A61K 39/00* (2006.01)
(52) U.S. Cl.
  CPC ...... *C07K 16/2809* (2013.01); *C07K 16/2818* (2013.01); *C07K 16/2851* (2013.01); *C07K 16/2878* (2013.01); *C07K 16/468* (2013.01); *A61K 2039/505* (2013.01); *A61K 2039/507* (2013.01); *C07K 2317/31* (2013.01); *C07K 2317/35* (2013.01); *C07K 2317/50* (2013.01); *C07K 2317/60* (2013.01); *C07K 2317/622* (2013.01); *C07K 2317/73* (2013.01); *C07K 2317/732* (2013.01); *C07K 2319/00* (2013.01)

(56) References Cited

FOREIGN PATENT DOCUMENTS

EP          2524699 A1    11/2012
JP       2007535915 A    12/2007

OTHER PUBLICATIONS

International Search Report and Written Opinion issued in corresponding PCT Application No. PCT/EP2016/055717, dated May 20, 2016; 15 pages.
Liao et al: "Preparation and Application of Anti-HBX/Anti-CD3 Bispecific Monoclonal Antibody (BSAB) Retargeting Effector Cells for Lysis of Human Hepatoma Xenografts in Nude Mice", Oncology Reports, vol. 3, No. 4; Jul. 1, 1996; pp. 637-644.
Jing Liu et al: "A New Format of Single Chain Tri-specific Antibody with Diminished Molecular Size Efficiently Induces Ovarian Tumor Cell Killing", Biotechnology Letters, Springer Netherlands, vol. 27, No. 22; pp. 1821-1827.
X.-B. Wang: "A New Recombinant Single Chain Trispecific Antibody Recruits T Lymphocytes to Kill CEA (Carcinoma Embryonic Antigen) Positive Tumor Cells In Vitro Efficiently", Journal of Biochemistry, vol. 135, No. 4, Apr. 1, 2004; pp. 555-565.
Schoonjans R et al: "Fab chains as an efficient heterodimerization scaffold forthe production of recombinant bispecific and trispecific antibody derivatives", The Journal of Immunology, The American Association of Immunologists, vol. 165, No. 12, Dec. 15, 2000; pp. 7050-7057.
Song Li-Ping et al: "A New Model of Trispecific Antibody With Cytotoxicity Against Tumor Cells", Shengwu Huaxue Yu Shengwu Wuli Xuebao-Acta Biochimica Et Biophysica Sinica, Shanghai Kexue Jishu Chubanshe, Shanghai, CN, vol. 35, No. 6, Jun. 1, 2003; pp. 503-510.
Jung G et al.: "Target Cell-Induced T Cell Activation With Bi- and Trispecific Anti Body Fragments", European Journal of Immunology, Wiley—V C H Verlag Gmbh & Co. KGAA, DE, vol. 21, Oct. 1, 1991; pp. 2431-2435.
Bohne et al.: "T Cells Redirected Against Hepatitis B Virus Surface Proteins Eliminate Infected Hepatocytes," Digestive Disease 2003; FL, Orlando; May 17-22, 2003, vol. 134, No. 1, Nov. 4, 2007; pp. 239-247.
Liu J. et al., A new format of single chain tri-specific antibody with diminished molecular size efficiently induces ovarian tumor cell killing, Biotechnology letters, 2005, pp. 1821-1827, vol. 27, No. 22.
Deyev S. M. et al., Multivalency: the hallmark of antibodies used for optimization of tumor targeting by design, Bioessays, 2008, pp. 904-918, vol. 30, No. 9.
Cuesta A. M. et al., Multivalent antibodies: when design surpasses evolution, Trends in Biotechnology, 2010, pp. 355-362, vol. 28, No. 7.
Kipriyanov S. M. et al., Generation and Production of Engineered Antibodies, Molecular Biotechnology, 2004, pp. 39-60, vol. 26, No. 1.
Souriau C. et al., Recombinant antibodies for cancer diagnosis and therapy, Expert Opinion on Biological Therapy, 2003, pp. 305-318, vol. 3, No. 2.
Chen X. et al., Fusion protein linkers: property, design and functionality, Advanced Drug Delivery Reviews, 2013, pp. 1357-1369, vol. 65, No. 10.
Maeda Y. et al., Engineering of Functional Chimeric Protein G-Vargula Luciferase, Analytical Biochemistry, 1997, pp. 147-152, vol. 249, No. 2.
Gasser B. et al., Antibody production with yeasts and filamentous fungi: on the road to large scale?, Biotechnology Letters, 2007, pp. 201-212, vol. 29.
Japanese Patent Office, Office Action issued in JP Patent Application No. 2017-546966, dated Sep. 24, 2019, pp. 1-6.

\* cited by examiner

A

B

A

B (I)

(II)

(III)

(IV)

(V)

(VI)

(VII)

SEQUENCE LISTING

```
<160> NUMBER OF SEQ ID NOS: 51

<210> SEQ ID NO 1
<211> LENGTH: 8
<212> TYPE: PRT
<213> ORGANISM: Artificial Sequence
<220> FEATURE:
<223> OTHER INFORMATION: CDR1 of scFv C8 heavy chain

<400> SEQUENCE: 1

Gly Phe Thr Phe Ser Gly Tyr Ala
1               5
```

<210> SEQ ID NO 2
<211> LENGTH: 8
<212> TYPE: PRT
<213> ORGANISM: Artificial Sequence
<220> FEATURE:
<223> OTHER INFORMATION: CDR2 of scFv C8 heavy chain

<400> SEQUENCE: 2

Ile Ser Gly Ser Gly Gly Ser Thr
1               5

<210> SEQ ID NO 3
<211> LENGTH: 21
<212> TYPE: PRT
<213> ORGANISM: Artificial Sequence
<220> FEATURE:
<223> OTHER INFORMATION: CDR3 of scFv C8 heavy chain

<400> SEQUENCE: 3

Ala Lys Pro Pro Gly Arg Gln Glu Tyr Tyr Gly Ser Ser Ile Tyr Tyr
1               5                   10                  15

Phe Pro Leu Gly Asn
            20

<210> SEQ ID NO 4
<211> LENGTH: 6
<212> TYPE: PRT
<213> ORGANISM: Artificial Sequence
<220> FEATURE:
<223> OTHER INFORMATION: CDR1 of scFv C8 light chain

<400> SEQUENCE: 4

Asn Ile Gly Ser Lys Ser
1               5

<210> SEQ ID NO 5
<211> LENGTH: 3
<212> TYPE: PRT
<213> ORGANISM: Artificial Sequence
<220> FEATURE:
<223> OTHER INFORMATION: CDR2 of scFv C8 light chain

<400> SEQUENCE: 5

Asp Asp Ser
1

<210> SEQ ID NO 6
<211> LENGTH: 11
<212> TYPE: PRT
<213> ORGANISM: Artificial Sequence
<220> FEATURE:
<223> OTHER INFORMATION: CDR3 of scFv C8 light chain

<400> SEQUENCE: 6

Gln Val Trp Asp Ser Ser Ser Asp Leu Val Val
1               5                   10

<210> SEQ ID NO 7
<211> LENGTH: 8
<212> TYPE: PRT
<213> ORGANISM: Artificial Sequence
<220> FEATURE:
<223> OTHER INFORMATION: CDR1 of scFv 5F9 heavy chain

<400> SEQUENCE: 7

-continued

Gly Phe Thr Phe Asn Asn Tyr Ala
1               5

<210> SEQ ID NO 8
<211> LENGTH: 8
<212> TYPE: PRT
<213> ORGANISM: Artificial Sequence
<220> FEATURE:
<223> OTHER INFORMATION: CDR2 of scFv 5F9 heavy chain

<400> SEQUENCE: 8

Ile Asn Ser Asp Gly Arg Ser Thr
1               5

<210> SEQ ID NO 9
<211> LENGTH: 8
<212> TYPE: PRT
<213> ORGANISM: Artificial Sequence
<220> FEATURE:
<223> OTHER INFORMATION: CDR3 of scFv 5F9 heavy chain

<400> SEQUENCE: 9

Ala Arg Thr Phe Tyr Ala Asp Tyr
1               5

<210> SEQ ID NO 10
<211> LENGTH: 6
<212> TYPE: PRT
<213> ORGANISM: Artificial Sequence
<220> FEATURE:
<223> OTHER INFORMATION: CDR1 of scFv 5F9 light chain

<400> SEQUENCE: 10

Gln Asn Val Asp Thr Thr
1               5

<210> SEQ ID NO 11
<211> LENGTH: 3
<212> TYPE: PRT
<213> ORGANISM: Artificial Sequence
<220> FEATURE:
<223> OTHER INFORMATION: CDR2 of scFv 5F9 light chain

<400> SEQUENCE: 11

Trp Ala Ser
1

<210> SEQ ID NO 12
<211> LENGTH: 9
<212> TYPE: PRT
<213> ORGANISM: Artificial Sequence
<220> FEATURE:
<223> OTHER INFORMATION: CDR3 of scFv 5F9 light chain

<400> SEQUENCE: 12

Gln Gln Tyr Ser Ile Phe Pro Tyr Thr
1               5

<210> SEQ ID NO 13
<211> LENGTH: 8
<212> TYPE: PRT
<213> ORGANISM: Artificial Sequence
<220> FEATURE:
<223> OTHER INFORMATION: CDR1 of scFv 5A19 heavy chain

<400> SEQUENCE: 13

Gly Phe Thr Phe Ser Ser Tyr Ala

<210> SEQ ID NO 14
<211> LENGTH: 8
<212> TYPE: PRT
<213> ORGANISM: Artificial Sequence
<220> FEATURE:
<223> OTHER INFORMATION: CDR2 of scFv 5A19 heavy chain

<400> SEQUENCE: 14

Val Ser Ser Asp Gly Ser Tyr Ala
1               5

<210> SEQ ID NO 15
<211> LENGTH: 9
<212> TYPE: PRT
<213> ORGANISM: Artificial Sequence
<220> FEATURE:
<223> OTHER INFORMATION: CDR3 of scFv 5A19 heavy chain

<400> SEQUENCE: 15

Ala Ser Phe Asn Trp Asp Val Ala Tyr
1               5

<210> SEQ ID NO 16
<211> LENGTH: 12
<212> TYPE: PRT
<213> ORGANISM: Artificial Sequence
<220> FEATURE:
<223> OTHER INFORMATION: CDR1 of scFv 5A19 light chain

<400> SEQUENCE: 16

Gln Ser Leu Leu Asn Thr Arg Thr Arg Lys Ser Tyr
1               5                   10

<210> SEQ ID NO 17
<211> LENGTH: 3
<212> TYPE: PRT
<213> ORGANISM: Artificial Sequence
<220> FEATURE:
<223> OTHER INFORMATION: CDR2 of scFv 5A19 light chain

<400> SEQUENCE: 17

Trp Ala Ser
1

<210> SEQ ID NO 18
<211> LENGTH: 8
<212> TYPE: PRT
<213> ORGANISM: Artificial Sequence
<220> FEATURE:
<223> OTHER INFORMATION: CDR3 of scFv 5A19 light chain

<400> SEQUENCE: 18

Lys Gln Ser Tyr Ser Leu Tyr Thr
1               5

<210> SEQ ID NO 19
<211> LENGTH: 8
<212> TYPE: PRT
<213> ORGANISM: Artificial Sequence
<220> FEATURE:
<223> OTHER INFORMATION: CDR1 of scFv OKT3 heavy chain

<400> SEQUENCE: 19

Gly Tyr Thr Phe Thr Arg Tyr Thr
1               5

```
<210> SEQ ID NO 20
<211> LENGTH: 8
<212> TYPE: PRT
<213> ORGANISM: Artificial Sequence
<220> FEATURE:
<223> OTHER INFORMATION: CDR2 of scFv OKT3 heavy chain

<400> SEQUENCE: 20

Ile Asn Pro Ser Arg Gly Tyr Thr
1               5

<210> SEQ ID NO 21
<211> LENGTH: 12
<212> TYPE: PRT
<213> ORGANISM: Artificial Sequence
<220> FEATURE:
<223> OTHER INFORMATION: CDR3 of scFv OKT3 heavy chain

<400> SEQUENCE: 21

Ala Arg Tyr Tyr Asp Asp His Tyr Cys Leu Asp Tyr
1               5                   10

<210> SEQ ID NO 22
<211> LENGTH: 5
<212> TYPE: PRT
<213> ORGANISM: Artificial Sequence
<220> FEATURE:
<223> OTHER INFORMATION: CDR1 of scFv OKT3 light chain

<400> SEQUENCE: 22

Ser Ser Val Ser Tyr
1               5

<210> SEQ ID NO 23
<211> LENGTH: 3
<212> TYPE: PRT
<213> ORGANISM: Artificial Sequence
<220> FEATURE:
<223> OTHER INFORMATION: CDR2 of scFv OKT3 light chain

<400> SEQUENCE: 23

Asp Thr Ser
1

<210> SEQ ID NO 24
<211> LENGTH: 9
<212> TYPE: PRT
<213> ORGANISM: Artificial Sequence
<220> FEATURE:
<223> OTHER INFORMATION: CDR3 of scFv OKT3 light chain

<400> SEQUENCE: 24

Gln Gln Trp Ser Ser Asn Pro Phe Thr
1               5

<210> SEQ ID NO 25
<211> LENGTH: 8
<212> TYPE: PRT
<213> ORGANISM: Artificial Sequence
<220> FEATURE:
<223> OTHER INFORMATION: CDR1 of scFv 9.3 heavy chain

<400> SEQUENCE: 25

Gly Phe Ser Leu Ser Asp Tyr Gly
1               5
```

<210> SEQ ID NO 26
<211> LENGTH: 7
<212> TYPE: PRT
<213> ORGANISM: Artificial Sequence
<220> FEATURE:
<223> OTHER INFORMATION: CDR2 of scFv 9.3 heavy chain

<400> SEQUENCE: 26

Ile Trp Ala Gly Gly Gly Thr
1               5

<210> SEQ ID NO 27
<211> LENGTH: 14
<212> TYPE: PRT
<213> ORGANISM: Artificial Sequence
<220> FEATURE:
<223> OTHER INFORMATION: CDR3 of scFv 9.3 heavy chain

<400> SEQUENCE: 27

Ala Arg Asp Lys Gly Tyr Ser Tyr Tyr Ser Met Asp Tyr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: CDR1 of scFv 9.3 light chain

<400> SEQUENCE: 28

Glu Ser Val Glu Tyr Tyr Val Thr Ser Leu
1               5                   10

<210> SEQ ID NO 29
<211> LENGTH: 3
<212> TYPE: PRT
<213> ORGANISM: Artificial Sequence
<220> FEATURE:
<223> OTHER INFORMATION: CDR2 of scFv 9.3 light chain

<400> SEQUENCE: 29

Ala Ala Ser
1

<210> SEQ ID NO 30
<211> LENGTH: 9
<212> TYPE: PRT
<213> ORGANISM: Artificial Sequence
<220> FEATURE:
<223> OTHER INFORMATION: CDR3 of scFv 9.3 light chain

<400> SEQUENCE: 30

Gln Gln Ser Arg Lys Val Pro Tyr Thr
1               5

<210> SEQ ID NO 31
<211> LENGTH: 8
<212> TYPE: PRT
<213> ORGANISM: Artificial Sequence
<220> FEATURE:
<223> OTHER INFORMATION: CDR1 of scFv A9 heavy chain

<400> SEQUENCE: 31

Gly Tyr Thr Phe Thr Asn Tyr Trp
1               5

```
<210> SEQ ID NO 32
<211> LENGTH: 8
<212> TYPE: PRT
<213> ORGANISM: Artificial Sequence
<220> FEATURE:
<223> OTHER INFORMATION: CDR2 of scFv A9 heavy chain

<400> SEQUENCE: 32

Ile Tyr Pro Gly Gly Gly Tyr Thr
1               5

<210> SEQ ID NO 33
<211> LENGTH: 10
<212> TYPE: PRT
<213> ORGANISM: Artificial Sequence
<220> FEATURE:
<223> OTHER INFORMATION: CDR3 of scFv A9 heavy chain

<400> SEQUENCE: 33

Ala Arg Ser Ala Ser Trp Tyr Phe Asp Val
1               5                   10

<210> SEQ ID NO 34
<211> LENGTH: 9
<212> TYPE: PRT
<213> ORGANISM: Artificial Sequence
<220> FEATURE:
<223> OTHER INFORMATION: CDR1 of scFv A9 light chain

<400> SEQUENCE: 34

Thr Gly Thr Val Thr Thr Ser Asn Tyr
1               5

<210> SEQ ID NO 35
<211> LENGTH: 3
<212> TYPE: PRT
<213> ORGANISM: Artificial Sequence
<220> FEATURE:
<223> OTHER INFORMATION: CDR2 of scFv A9 light chain

<400> SEQUENCE: 35

His Thr Asn
1

<210> SEQ ID NO 36
<211> LENGTH: 9
<212> TYPE: PRT
<213> ORGANISM: Artificial Sequence
<220> FEATURE:
<223> OTHER INFORMATION: CDR3 of scFv A9 light chain

<400> SEQUENCE: 36

Ala Leu Trp Tyr Asn Asn His Trp Val
1               5

<210> SEQ ID NO 37
<211> LENGTH: 8
<212> TYPE: PRT
<213> ORGANISM: Artificial Sequence
<220> FEATURE:
<223> OTHER INFORMATION: CDR1 of scFv NCAM29.2 heavy chain

<400> SEQUENCE: 37

Gly Phe Thr Phe Ser Ser Phe Gly
1               5

<210> SEQ ID NO 38
```

```
<211> LENGTH: 8
<212> TYPE: PRT
<213> ORGANISM: Artificial Sequence
<220> FEATURE:
<223> OTHER INFORMATION: CDR2 of scFv NCAM29.2 heavy chain

<400> SEQUENCE: 38

Ile Ser Ser Gly Ser Tyr Ala Ile
1               5

<210> SEQ ID NO 39
<211> LENGTH: 14
<212> TYPE: PRT
<213> ORGANISM: Artificial Sequence
<220> FEATURE:
<223> OTHER INFORMATION: CDR3 of scFv NCAM29.2 heavy chain

<400> SEQUENCE: 39

Val Arg Gly Arg Arg Leu Gly Glu Gly Tyr Ala Met Asp Tyr
1               5                   10

<210> SEQ ID NO 40
<211> LENGTH: 12
<212> TYPE: PRT
<213> ORGANISM: Artificial Sequence
<220> FEATURE:
<223> OTHER INFORMATION: CDR1 of scFv NCAM29.2 light chain

<400> SEQUENCE: 40

Gln Ser Leu Leu Tyr Ser Ser Asn Gln Lys Asn Tyr
1               5                   10

<210> SEQ ID NO 41
<211> LENGTH: 3
<212> TYPE: PRT
<213> ORGANISM: Artificial Sequence
<220> FEATURE:
<223> OTHER INFORMATION: CDR2 of scFv NCAM29.2 light chain

<400> SEQUENCE: 41

Trp Ala Ser
1

<210> SEQ ID NO 42
<211> LENGTH: 7
<212> TYPE: PRT
<213> ORGANISM: Artificial Sequence
<220> FEATURE:
<223> OTHER INFORMATION: CDR3 of scFv NCAM29.2 light chain

<400> SEQUENCE: 42

Gln Gln Tyr Ser Ser Trp Thr
1               5

<210> SEQ ID NO 43
<211> LENGTH: 794
<212> TYPE: PRT
<213> ORGANISM: Artificial Sequence
<220> FEATURE:
<223> OTHER INFORMATION: Anti-HBsAg scFv [C8]^Glycin-Serin-Linker^hIgG1-
      Fc[C245S,L259F,L260E,G262A,A355T]^StrepTag^Glycin-Linker^anti-CD3
      scFv [OKT3]

<400> SEQUENCE: 43

Met Asp Phe Glu Val Gln Ile Phe Ser Phe Leu Leu Ile Ser Ala Ser
1               5                   10                  15

Val Ile Met Ser Arg Met Ala Glu Val Gln Leu Val Glu Ser Gly Gly
```

```
                20                  25                  30
Gly Leu Leu Gln Pro Gly Gly Ser Leu Arg Leu Ser Cys Ala Ala Ser
             35                  40                  45

Gly Phe Thr Phe Ser Gly Tyr Ala Met Ser Trp Val Arg Gln Ala Pro
 50                  55                  60

Gly Lys Gly Leu Glu Trp Val Ser Ser Ile Ser Gly Ser Gly Gly Ser
 65                  70                  75                  80

Thr Tyr Tyr Ala Asp Ser Val Lys Gly Arg Phe Thr Ile Ser Arg Asp
                 85                  90                  95

Asn Ser Lys Asn Thr Leu Tyr Leu Gln Met Asn Ser Leu Arg Ala Glu
                100                 105                 110

Asp Thr Ala Leu Tyr Tyr Cys Ala Lys Pro Pro Gly Arg Gln Glu Tyr
                115                 120                 125

Tyr Gly Ser Ser Ile Tyr Tyr Phe Pro Leu Gly Asn Trp Gly Gln Gly
                130                 135                 140

Thr Leu Val Thr Val Ser Ser Ala Ser Thr Lys Gly Pro Lys Leu Glu
145                 150                 155                 160

Glu Gly Glu Phe Ser Glu Ala Arg Val Gln Ser Ala Leu Thr Gln Pro
                165                 170                 175

Ala Ser Val Ser Val Ala Pro Gly Gln Thr Ala Arg Ile Thr Cys Gly
                180                 185                 190

Gly Asn Asn Ile Gly Ser Lys Ser Val His Trp Tyr Gln Gln Lys Pro
                195                 200                 205

Gly Gln Ala Pro Val Leu Val Val Tyr Asp Asp Ser Asp Arg Pro Ser
                210                 215                 220

Gly Ile Pro Glu Arg Phe Ser Gly Ser Asn Ser Gly Asn Thr Ala Thr
225                 230                 235                 240

Leu Thr Ile Ser Arg Val Glu Ala Gly Asp Glu Ala Asp Tyr Tyr Cys
                245                 250                 255

Gln Val Trp Asp Ser Ser Ser Asp Leu Val Val Phe Gly Gly Gly Thr
                260                 265                 270

Lys Leu Thr Val Leu Gly Asn Ser Gly Gly Gly Gly Ser Gly Gly Gly
                275                 280                 285

Gly Ser Gly Gly Gly Ser Ala Ser Glu Pro Lys Ser Ser Asp Lys
290                 295                 300

Thr His Thr Cys Pro Pro Cys Pro Ala Pro Glu Phe Glu Gly Ala Pro
305                 310                 315                 320

Ser Val Phe Leu Phe Pro Pro Lys Pro Lys Asp Thr Leu Met Ile Ser
                325                 330                 335

Arg Thr Pro Glu Val Thr Cys Val Val Val Asp Val Ser His Glu Asp
                340                 345                 350

Pro Glu Val Lys Phe Asn Trp Tyr Val Asp Gly Val Glu Val His Asn
                355                 360                 365

Ala Lys Thr Lys Pro Arg Glu Glu Gln Tyr Asn Ser Thr Tyr Arg Val
                370                 375                 380

Val Ser Val Leu Thr Val Leu His Gln Asp Trp Leu Asn Gly Lys Glu
385                 390                 395                 400

Tyr Lys Cys Lys Val Ser Asn Lys Ala Leu Pro Thr Pro Ile Glu Lys
                405                 410                 415

Thr Ile Ser Lys Ala Lys Gly Gln Pro Arg Glu Pro Gln Val Tyr Thr
                420                 425                 430

Leu Pro Pro Ser Arg Asp Glu Leu Thr Lys Asn Gln Val Ser Leu Thr
                435                 440                 445
```

Cys Leu Val Lys Gly Phe Tyr Pro Ser Asp Ile Ala Val Glu Trp Glu
    450                 455                 460

Ser Asn Gly Gln Pro Glu Asn Asn Tyr Lys Thr Thr Pro Pro Val Leu
465                 470                 475                 480

Asp Ser Asp Gly Ser Phe Phe Leu Tyr Ser Lys Leu Thr Val Asp Lys
                485                 490                 495

Ser Arg Trp Gln Gln Gly Asn Val Phe Ser Cys Ser Val Met His Glu
            500                 505                 510

Ala Leu His Asn His Tyr Thr Gln Lys Ser Leu Ser Leu Ser Pro Gly
        515                 520                 525

Lys Asp Pro Gly Trp Ser His Pro Gln Phe Glu Lys Ser Arg Gly Gly
530                 535                 540

Gly Gly Gln Val Gln Leu Gln Gln Ser Gly Ala Glu Leu Ala Arg Pro
545                 550                 555                 560

Gly Ala Ser Val Lys Met Ser Cys Lys Ala Ser Gly Tyr Thr Phe Thr
                565                 570                 575

Arg Tyr Thr Met His Trp Val Lys Gln Arg Pro Gly Gln Gly Leu Glu
            580                 585                 590

Trp Ile Gly Tyr Ile Asn Pro Ser Arg Gly Tyr Thr Asn Tyr Asn Gln
        595                 600                 605

Lys Phe Lys Asp Lys Ala Thr Leu Thr Thr Asp Lys Ser Ser Ser Thr
610                 615                 620

Ala Tyr Met Gln Leu Ser Ser Leu Thr Ser Glu Asp Ser Ala Val Tyr
625                 630                 635                 640

Tyr Cys Ala Arg Tyr Tyr Asp Asp His Tyr Cys Leu Asp Tyr Trp Gly
                645                 650                 655

Gln Gly Thr Thr Leu Thr Val Ser Ser Gly Asn Ser Gly Gly Gly Gly
            660                 665                 670

Ser Gly Gly Gly Gly Ser Gly Gly Gly Ser Ala Ser Gln Ile Val
        675                 680                 685

Leu Thr Gln Ser Pro Ala Ile Met Ser Ala Ser Pro Gly Glu Lys Val
690                 695                 700

Thr Met Thr Cys Ser Ala Ser Ser Ser Val Ser Tyr Met Asn Trp Tyr
705                 710                 715                 720

Gln Gln Lys Ser Gly Thr Ser Pro Lys Arg Trp Ile Tyr Asp Thr Ser
                725                 730                 735

Lys Leu Ala Ser Gly Val Pro Ala His Phe Arg Gly Ser Gly Ser Gly
            740                 745                 750

Thr Ser Tyr Ser Leu Thr Ile Ser Gly Met Glu Ala Glu Asp Ala Ala
        755                 760                 765

Thr Tyr Tyr Cys Gln Gln Trp Ser Ser Asn Pro Phe Thr Phe Gly Ser
770                 775                 780

Gly Thr Lys Leu Glu Ile Asn Gly Asn Ser
785                 790

<210> SEQ ID NO 44
<211> LENGTH: 793
<212> TYPE: PRT
<213> ORGANISM: Artificial Sequence
<220> FEATURE:
<223> OTHER INFORMATION: Anti-HBsAg scFv [C8]^Glycin-Serin-Linker^hIgG1-
    Fc[C245S,L259F,L260E,G262A,A355T]^StrepTag^Glycin-Linker^ anti-
    CD28 scFv [9.3]

<400> SEQUENCE: 44

```
Met Asp Phe Glu Val Gln Ile Phe Ser Phe Leu Leu Ile Ser Ala Ser
1               5                   10                  15

Val Ile Met Ser Arg Met Ala Glu Val Gln Leu Val Glu Ser Gly Gly
                20                  25                  30

Gly Leu Leu Gln Pro Gly Gly Ser Leu Arg Leu Ser Cys Ala Ala Ser
            35                  40                  45

Gly Phe Thr Phe Ser Gly Tyr Ala Met Ser Trp Val Arg Gln Ala Pro
        50                  55                  60

Gly Lys Gly Leu Glu Trp Val Ser Ser Ile Ser Gly Ser Gly Gly Ser
65                  70                  75                  80

Thr Tyr Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Leu Tyr Tyr Cys Ala Lys Pro Pro Gly Arg Gln Glu Tyr
        115                 120                 125

Tyr Gly Ser Ser Ile Tyr Tyr Phe Pro Leu Gly Asn Trp Gly Gln Gly
    130                 135                 140

Thr Leu Val Thr Val Ser Ser Ala Ser Thr Lys Gly Pro Lys Leu Glu
145                 150                 155                 160

Glu Gly Glu Phe Ser Glu Ala Arg Val Gln Ser Ala Leu Thr Gln Pro
                165                 170                 175

Ala Ser Val Ser Val Ala Pro Gly Gln Thr Ala Arg Ile Thr Cys Gly
            180                 185                 190

Gly Asn Asn Ile Gly Ser Lys Ser Val His Trp Tyr Gln Gln Lys Pro
        195                 200                 205

Gly Gln Ala Pro Val Leu Val Val Tyr Asp Asp Ser Asp Arg Pro Ser
    210                 215                 220

Gly Ile Pro Glu Arg Phe Ser Gly Ser Asn Ser Gly Asn Thr Ala Thr
225                 230                 235                 240

Leu Thr Ile Ser Arg Val Glu Ala Gly Asp Glu Ala Asp Tyr Tyr Cys
                245                 250                 255

Gln Val Trp Asp Ser Ser Ser Asp Leu Val Val Phe Gly Gly Gly Thr
            260                 265                 270

Lys Leu Thr Val Leu Gly Asn Ser Gly Gly Gly Ser Gly Gly Gly Gly
        275                 280                 285

Gly Ser Gly Gly Gly Ser Ala Ser Glu Pro Lys Ser Ser Asp Lys
    290                 295                 300

Thr His Thr Cys Pro Pro Cys Pro Ala Pro Glu Phe Glu Gly Ala Pro
305                 310                 315                 320

Ser Val Phe Leu Phe Pro Pro Lys Pro Lys Asp Thr Leu Met Ile Ser
                325                 330                 335

Arg Thr Pro Glu Val Thr Cys Val Val Val Asp Val Ser His Glu Asp
            340                 345                 350

Pro Glu Val Lys Phe Asn Trp Tyr Val Asp Gly Val Glu Val His Asn
        355                 360                 365

Ala Lys Thr Lys Pro Arg Glu Glu Gln Tyr Asn Ser Thr Tyr Arg Val
    370                 375                 380

Val Ser Val Leu Thr Val Leu His Gln Asp Trp Leu Asn Gly Lys Glu
385                 390                 395                 400

Tyr Lys Cys Lys Val Ser Asn Lys Ala Leu Pro Thr Pro Ile Glu Lys
                405                 410                 415

Thr Ile Ser Lys Ala Lys Gly Gln Pro Arg Glu Pro Gln Val Tyr Thr
```

```
                420             425             430
Leu Pro Pro Ser Arg Asp Glu Leu Thr Lys Asn Gln Val Ser Leu Thr
            435             440             445
Cys Leu Val Lys Gly Phe Tyr Pro Ser Asp Ile Ala Val Glu Trp Glu
            450             455             460
Ser Asn Gly Gln Pro Glu Asn Asn Tyr Lys Thr Thr Pro Pro Val Leu
465             470             475             480
Asp Ser Asp Gly Ser Phe Phe Leu Tyr Ser Lys Leu Thr Val Asp Lys
            485             490             495
Ser Arg Trp Gln Gln Gly Asn Val Phe Ser Cys Ser Val Met His Glu
            500             505             510
Ala Leu His Asn His Tyr Thr Gln Lys Ser Leu Ser Leu Ser Pro Gly
            515             520             525
Lys Asp Pro Gly Trp Ser His Pro Gln Phe Glu Lys Ser Ser Gly Gly
            530             535             540
Gly Gly Gln Val Gln Leu Gln Glu Ser Gly Pro Gly Leu Val Thr Pro
545             550             555             560
Ser Gln Ser Leu Ser Ile Thr Cys Thr Val Ser Gly Phe Ser Leu Ser
            565             570             575
Asp Tyr Gly Val His Trp Val Arg Gln Ser Pro Gly Gln Gly Leu Glu
            580             585             590
Trp Leu Gly Val Ile Trp Ala Gly Gly Thr Asn Tyr Asn Ser Ala
            595             600             605
Leu Met Ser Arg Lys Ser Ile Ser Lys Asp Asn Ser Lys Ser Gln Val
            610             615             620
Phe Leu Lys Met Asn Ser Leu Gln Ala Asp Asp Thr Ala Val Tyr Tyr
625             630             635             640
Cys Ala Arg Asp Lys Gly Tyr Ser Tyr Tyr Tyr Ser Met Asp Tyr Trp
            645             650             655
Gly Gln Gly Thr Thr Val Thr Val Ser Ser Arg Gly Gly Gly Ser Gly
            660             665             670
Gly Gly Gly Ser Gly Gly Gly Ser Asp Ile Glu Leu Thr Gln Ser
            675             680             685
Pro Ala Ser Leu Ala Val Ser Leu Gly Gln Arg Ala Thr Ile Ser Cys
            690             695             700
Arg Ala Ser Glu Ser Val Glu Tyr Tyr Val Thr Ser Leu Met Gln Trp
705             710             715             720
Tyr Gln Gln Lys Pro Gly Gln Pro Pro Lys Leu Leu Ile Phe Ala Ala
            725             730             735
Ser Asn Val Glu Ser Gly Val Pro Ala Arg Phe Ser Gly Ser Gly Ser
            740             745             750
Gly Thr Asn Phe Ser Leu Asn Ile His Pro Val Asp Glu Asp Val
            755             760             765
Ala Met Tyr Phe Cys Gln Gln Ser Arg Lys Val Pro Tyr Thr Phe Gly
            770             775             780
Gly Gly Thr Lys Leu Glu Ile Lys Arg
785             790

<210> SEQ ID NO 45
<211> LENGTH: 792
<212> TYPE: PRT
<213> ORGANISM: Artificial Sequence
<220> FEATURE:
<223> OTHER INFORMATION: Anti-HBsAg scFv [C8]^Glycin-Serin-Linker^hIgG1-
      Fc[C245S,L259F,L260E,G StrepTag^anti-CD16 scFv [A9]

<400> SEQUENCE: 45

```
Met Asp Phe Glu Val Gln Ile Phe Ser Phe Leu Leu Ile Ser Ala Ser
1               5                   10                  15

Val Ile Met Ser Arg Met Ala Glu Val Gln Leu Val Glu Ser Gly Gly
            20                  25                  30

Gly Leu Leu Gln Pro Gly Gly Ser Leu Arg Leu Ser Cys Ala Ala Ser
        35                  40                  45

Gly Phe Thr Phe Ser Gly Tyr Ala Met Ser Trp Val Arg Gln Ala Pro
    50                  55                  60

Gly Lys Gly Leu Glu Trp Val Ser Ser Ile Ser Gly Ser Gly Gly Ser
65                  70                  75                  80

Thr Tyr Tyr Ala Asp Ser Val Lys Gly Arg Phe Thr Ile Ser Arg Asp
            85                  90                  95

Asn Ser Lys Asn Thr Leu Tyr Leu Gln Met Asn Ser Leu Arg Ala Glu
        100                 105                 110

Asp Thr Ala Leu Tyr Tyr Cys Ala Lys Pro Pro Gly Arg Gln Glu Tyr
    115                 120                 125

Tyr Gly Ser Ser Ile Tyr Tyr Phe Pro Leu Gly Asn Trp Gly Gln Gly
130                 135                 140

Thr Leu Val Thr Val Ser Ser Ala Ser Thr Lys Gly Pro Lys Leu Glu
145                 150                 155                 160

Glu Gly Glu Phe Ser Glu Ala Arg Val Gln Ser Ala Leu Thr Gln Pro
            165                 170                 175

Ala Ser Val Ser Val Ala Pro Gly Gln Thr Ala Arg Ile Thr Cys Gly
        180                 185                 190

Gly Asn Asn Ile Gly Ser Lys Ser Val His Trp Tyr Gln Gln Lys Pro
    195                 200                 205

Gly Gln Ala Pro Val Leu Val Val Tyr Asp Asp Ser Asp Arg Pro Ser
210                 215                 220

Gly Ile Pro Glu Arg Phe Ser Gly Ser Asn Ser Gly Asn Thr Ala Thr
225                 230                 235                 240

Leu Thr Ile Ser Arg Val Glu Ala Gly Asp Glu Ala Asp Tyr Tyr Cys
            245                 250                 255

Gln Val Trp Asp Ser Ser Ser Asp Leu Val Val Phe Gly Gly Gly Thr
        260                 265                 270

Lys Leu Thr Val Leu Gly Asn Ser Gly Gly Gly Ser Gly Gly Gly Gly
    275                 280                 285

Gly Ser Gly Gly Gly Ser Ala Ser Glu Pro Lys Ser Ser Asp Lys
    290                 295                 300

Thr His Thr Cys Pro Pro Cys Pro Ala Pro Glu Phe Glu Gly Ala Pro
305                 310                 315                 320

Ser Val Phe Leu Phe Pro Pro Lys Pro Lys Asp Thr Leu Met Ile Ser
            325                 330                 335

Arg Thr Pro Glu Val Thr Cys Val Val Val Asp Val Ser His Glu Asp
        340                 345                 350

Pro Glu Val Lys Phe Asn Trp Tyr Val Asp Gly Val Glu Val His Asn
    355                 360                 365

Ala Lys Thr Lys Pro Arg Glu Glu Gln Tyr Asn Ser Thr Tyr Arg Val
    370                 375                 380

Val Ser Val Leu Thr Val Leu His Gln Asp Trp Leu Asn Gly Lys Glu
385                 390                 395                 400
```

```
Tyr Lys Cys Lys Val Ser Asn Lys Ala Leu Pro Thr Pro Ile Glu Lys
                405                 410                 415
Thr Ile Ser Lys Ala Lys Gly Gln Pro Arg Glu Pro Gln Val Tyr Thr
            420                 425                 430
Leu Pro Pro Ser Arg Asp Glu Leu Thr Lys Asn Gln Val Ser Leu Thr
        435                 440                 445
Cys Leu Val Lys Gly Phe Tyr Pro Ser Asp Ile Ala Val Glu Trp Glu
450                 455                 460
Ser Asn Gly Gln Pro Glu Asn Asn Tyr Lys Thr Thr Pro Pro Val Leu
465                 470                 475                 480
Asp Ser Asp Gly Ser Phe Phe Leu Tyr Ser Lys Leu Thr Val Asp Lys
                485                 490                 495
Ser Arg Trp Gln Gln Gly Asn Val Phe Ser Cys Ser Val Met His Glu
            500                 505                 510
Ala Leu His Asn His Tyr Thr Gln Lys Ser Leu Ser Leu Ser Pro Gly
        515                 520                 525
Lys Asp Pro Gly Trp Ser His Pro Gln Phe Glu Lys Ser Arg Gly Gly
530                 535                 540
Gly Gly Gln Val Gln Leu Gln Gln Ser Gly Ala Glu Leu Val Arg Pro
545                 550                 555                 560
Gly Thr Ser Val Lys Ile Ser Cys Lys Ala Ser Gly Tyr Thr Phe Thr
                565                 570                 575
Asn Tyr Trp Leu Gly Trp Val Lys Gln Arg Pro Gly His Gly Leu Glu
            580                 585                 590
Trp Ile Gly Asp Ile Tyr Pro Gly Gly Gly Tyr Thr Asn Tyr Asn Glu
        595                 600                 605
Lys Phe Lys Gly Lys Ala Thr Val Thr Ala Asp Thr Ser Ser Arg Thr
610                 615                 620
Ala Tyr Val Gln Val Arg Ser Leu Thr Ser Glu Asp Ser Ala Val Tyr
625                 630                 635                 640
Phe Cys Ala Arg Ser Ala Ser Trp Tyr Phe Asp Val Trp Gly Ala Gly
                645                 650                 655
Thr Thr Val Thr Val Ser Ser Gly Asn Ser Gly Gly Gly Gly Ser Gly
            660                 665                 670
Gly Gly Ser Gly Gly Gly Ser Ala Ser Gln Ala Val Val Thr
        675                 680                 685
Gln Glu Ser Ala Leu Thr Thr Ser Pro Gly Glu Thr Val Thr Leu Thr
690                 695                 700
Cys Arg Ser Asn Thr Gly Thr Val Thr Thr Ser Asn Tyr Ala Asn Trp
705                 710                 715                 720
Val Gln Glu Lys Pro Asp His Leu Phe Thr Gly Leu Ile Gly His Thr
                725                 730                 735
Asn Asn Arg Ala Pro Gly Val Pro Ala Arg Phe Ser Gly Ser Leu Ile
            740                 745                 750
Gly Asp Lys Ala Ala Leu Thr Ile Thr Gly Ala Gln Thr Glu Asp Glu
        755                 760                 765
Ala Ile Tyr Phe Cys Ala Leu Trp Tyr Asn Asn His Trp Val Phe Gly
770                 775                 780
Gly Gly Thr Lys Leu Thr Val Leu
785                 790
```

<210> SEQ ID NO 46
<211> LENGTH: 799
<212> TYPE: PRT

<213> ORGANISM: Artificial Sequence
<220> FEATURE:
<223> OTHER INFORMATION: Anti-HBsAg scFv [C8]^Glycin-Serin-Linker^hIgG1-
      Fc[C245S,L259F,L260E,G262A,A355T]^StrepTag^Glycin-Linker^
      StrepTag^anti-CD56 scFv [NCAM29.2]

<400> SEQUENCE: 46

```
Met Asp Phe Glu Val Gln Ile Phe Ser Phe Leu Leu Ile Ser Ala Ser
1               5                   10                  15
Val Ile Met Ser Arg Met Ala Glu Val Gln Leu Val Glu Ser Gly Gly
            20                  25                  30
Gly Leu Leu Gln Pro Gly Gly Ser Leu Arg Leu Ser Cys Ala Ala Ser
        35                  40                  45
Gly Phe Thr Phe Ser Gly Tyr Ala Met Ser Trp Val Arg Gln Ala Pro
    50                  55                  60
Gly Lys Gly Leu Glu Trp Val Ser Ser Ile Ser Gly Ser Gly Gly Ser
65                  70                  75                  80
Thr Tyr Tyr Ala Asp Ser Val Lys Gly Arg Phe Thr Ile Ser Arg Asp
                85                  90                  95
Asn Ser Lys Asn Thr Leu Tyr Leu Gln Met Asn Ser Leu Arg Ala Glu
            100                 105                 110
Asp Thr Ala Leu Tyr Tyr Cys Ala Lys Pro Pro Gly Arg Gln Glu Tyr
        115                 120                 125
Tyr Gly Ser Ser Ile Tyr Tyr Phe Pro Leu Gly Asn Trp Gly Gln Gly
    130                 135                 140
Thr Leu Val Thr Val Ser Ser Ala Ser Thr Lys Gly Pro Lys Leu Glu
145                 150                 155                 160
Glu Gly Glu Phe Ser Glu Ala Arg Val Gln Ser Ala Leu Thr Gln Pro
                165                 170                 175
Ala Ser Val Ser Val Ala Pro Gly Gln Thr Ala Arg Ile Thr Cys Gly
            180                 185                 190
Gly Asn Asn Ile Gly Ser Lys Ser Val His Trp Tyr Gln Gln Lys Pro
        195                 200                 205
Gly Gln Ala Pro Val Leu Val Val Tyr Asp Asp Ser Asp Arg Pro Ser
    210                 215                 220
Gly Ile Pro Glu Arg Phe Ser Gly Ser Asn Ser Gly Asn Thr Ala Thr
225                 230                 235                 240
Leu Thr Ile Ser Arg Val Glu Ala Gly Asp Glu Ala Asp Tyr Tyr Cys
                245                 250                 255
Gln Val Trp Asp Ser Ser Ser Asp Leu Val Val Phe Gly Gly Gly Thr
            260                 265                 270
Lys Leu Thr Val Leu Gly Asn Ser Gly Gly Gly Ser Gly Gly Gly
        275                 280                 285
Gly Ser Gly Gly Gly Ser Ala Ser Glu Pro Lys Ser Ser Asp Lys
    290                 295                 300
Thr His Thr Cys Pro Pro Cys Pro Ala Pro Glu Phe Glu Gly Ala Pro
305                 310                 315                 320
Ser Val Phe Leu Phe Pro Pro Lys Pro Lys Asp Thr Leu Met Ile Ser
                325                 330                 335
Arg Thr Pro Glu Val Thr Cys Val Val Asp Val Ser His Glu Asp
            340                 345                 350
Pro Glu Val Lys Phe Asn Trp Tyr Val Asp Gly Val Glu Val His Asn
        355                 360                 365
Ala Lys Thr Lys Pro Arg Glu Glu Gln Tyr Asn Ser Thr Tyr Arg Val
    370                 375                 380
```

```
Val Ser Val Leu Thr Val Leu His Gln Asp Trp Leu Asn Gly Lys Glu
385                 390                 395                 400

Tyr Lys Cys Lys Val Ser Asn Lys Ala Leu Pro Thr Pro Ile Glu Lys
                405                 410                 415

Thr Ile Ser Lys Ala Lys Gly Gln Pro Arg Glu Pro Gln Val Tyr Thr
            420                 425                 430

Leu Pro Pro Ser Arg Asp Glu Leu Thr Lys Asn Gln Val Ser Leu Thr
            435                 440                 445

Cys Leu Val Lys Gly Phe Tyr Pro Ser Asp Ile Ala Val Glu Trp Glu
        450                 455                 460

Ser Asn Gly Gln Pro Glu Asn Asn Tyr Lys Thr Thr Pro Pro Val Leu
465                 470                 475                 480

Asp Ser Asp Gly Ser Phe Phe Leu Tyr Ser Lys Leu Thr Val Asp Lys
                485                 490                 495

Ser Arg Trp Gln Gln Gly Asn Val Phe Ser Cys Ser Val Met His Glu
            500                 505                 510

Ala Leu His Asn His Tyr Thr Gln Lys Ser Leu Ser Leu Ser Pro Gly
        515                 520                 525

Lys Asp Pro Gly Trp Ser His Pro Gln Phe Glu Lys Ser Ser Gly Gly
530                 535                 540

Gly Gly Asp Val Gln Leu Val Glu Ser Gly Gly Leu Val Gln Pro
545                 550                 555                 560

Gly Gly Ser Arg Lys Leu Ser Cys Ala Ala Ser Gly Phe Thr Phe Ser
                565                 570                 575

Ser Phe Gly Met His Trp Val Arg Gln Ala Pro Glu Lys Gly Leu Glu
            580                 585                 590

Trp Val Ala Tyr Ile Ser Ser Gly Ser Tyr Ala Ile Tyr Tyr Ala Asp
        595                 600                 605

Thr Val Lys Gly Arg Phe Thr Ile Ser Arg Asp Asn Pro Glu Asn Thr
610                 615                 620

Leu Phe Leu Gln Met Thr Ser Leu Arg Ser Glu Asp Ser Ala Met Tyr
625                 630                 635                 640

Tyr Cys Val Arg Gly Arg Arg Leu Gly Glu Gly Tyr Ala Met Asp Tyr
                645                 650                 655

Trp Gly Gln Gly Thr Ser Val Thr Val Ser Ser Gly Asn Ser Gly Gly
            660                 665                 670

Gly Gly Ser Gly Gly Gly Gly Ser Gly Gly Gly Gly Ser Ala Ser Asp
        675                 680                 685

Ile Val Met Ser Gln Ser Pro Ser Ser Leu Ala Val Ser Val Gly Glu
        690                 695                 700

Lys Val Thr Met Ser Cys Lys Ser Ser Gln Ser Leu Leu Tyr Ser Ser
705                 710                 715                 720

Asn Gln Lys Asn Tyr Leu Ala Trp Tyr Gln Gln Lys Pro Gly Gln Ser
                725                 730                 735

Pro Lys Leu Leu Ile Tyr Trp Ala Ser Thr Arg Lys Ser Gly Val Pro
            740                 745                 750

Asp Arg Phe Thr Gly Ser Gly Ser Gly Thr Asp Phe Thr Leu Thr Ile
            755                 760                 765

Ser Ser Val Lys Ala Glu Asp Leu Ala Val Tyr Tyr Cys Gln Gln Tyr
        770                 775                 780

Ser Ser Trp Thr Phe Gly Gly Gly Thr Lys Leu Glu Ile Lys Arg
785                 790                 795
```

<210> SEQ ID NO 47
<211> LENGTH: 15
<212> TYPE: PRT
<213> ORGANISM: Artificial Sequence
<220> FEATURE:
<223> OTHER INFORMATION: Linker

<400> SEQUENCE: 47

Gly Gly Gly Gly Ser Gly Gly Gly Gly Ser Gly Gly Gly Gly Ser
1               5                   10                  15

<210> SEQ ID NO 48
<211> LENGTH: 17
<212> TYPE: PRT
<213> ORGANISM: Artificial Sequence
<220> FEATURE:
<223> OTHER INFORMATION: Linker

<400> SEQUENCE: 48

Ala Lys Thr Thr Pro Lys Leu Glu Glu Gly Glu Phe Ser Glu Ala Arg
1               5                   10                  15

Val

<210> SEQ ID NO 49
<211> LENGTH: 20
<212> TYPE: PRT
<213> ORGANISM: Artificial Sequence
<220> FEATURE:
<223> OTHER INFORMATION: Linker

<400> SEQUENCE: 49

Gly Gly Gly Gly Ser Gly Gly Gly Gly Ser Gly Gly Gly Gly Ser Gly
1               5                   10                  15

Gly Gly Gly Ser
            20

<210> SEQ ID NO 50
<211> LENGTH: 835
<212> TYPE: PRT
<213> ORGANISM: Artificial Sequence
<220> FEATURE:
<223> OTHER INFORMATION: C8-hIgG1Fcmut-OKT3 with Jun leucine zipper
      dimerization domain

<400> SEQUENCE: 50

Met Asp Phe Glu Val Gln Ile Phe Ser Phe Leu Leu Ile Ser Ala Ser
1               5                   10                  15

Val Ile Met Ser Arg Met Ala Glu Val Gln Leu Val Glu Ser Gly Gly
                20                  25                  30

Gly Leu Leu Gln Pro Gly Gly Ser Leu Arg Leu Ser Cys Ala Ala Ser
            35                  40                  45

Gly Phe Thr Phe Ser Gly Tyr Ala Met Ser Trp Val Arg Gln Ala Pro
        50                  55                  60

Gly Lys Gly Leu Glu Trp Val Ser Ser Ile Ser Gly Ser Gly Gly Ser
65                  70                  75                  80

Thr Tyr Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Leu Tyr Tyr Cys Ala Lys Pro Pro Gly Arg Gln Glu Tyr
        115                 120                 125

```
Tyr Gly Ser Ser Ile Tyr Tyr Phe Pro Leu Gly Asn Trp Gly Gln Gly
    130                 135                 140

Thr Leu Val Thr Val Ser Ser Ala Ser Thr Lys Gly Pro Lys Leu Glu
145                 150                 155                 160

Glu Gly Glu Phe Ser Glu Ala Arg Val Gln Ser Ala Leu Thr Gln Pro
                165                 170                 175

Ala Ser Val Ser Val Ala Pro Gly Gln Thr Ala Arg Ile Thr Cys Gly
            180                 185                 190

Gly Asn Asn Ile Gly Ser Lys Ser Val His Trp Tyr Gln Gln Lys Pro
        195                 200                 205

Gly Gln Ala Pro Val Leu Val Val Tyr Asp Asp Ser Asp Arg Pro Ser
    210                 215                 220

Gly Ile Pro Glu Arg Phe Ser Gly Ser Asn Ser Gly Asn Thr Ala Thr
225                 230                 235                 240

Leu Thr Ile Ser Arg Val Glu Ala Gly Asp Glu Ala Asp Tyr Tyr Cys
                245                 250                 255

Gln Val Trp Asp Ser Ser Ser Asp Leu Val Val Phe Gly Gly Gly Thr
            260                 265                 270

Lys Leu Thr Val Leu Gly Asn Ser Gly Gly Gly Ser Gly Gly Gly
        275                 280                 285

Gly Ser Gly Gly Gly Ser Ala Ser Arg Ile Ala Arg Leu Glu Glu
    290                 295                 300

Lys Val Lys Thr Leu Lys Ala Gln Asn Ser Glu Leu Ala Ser Thr Ala
305                 310                 315                 320

Asn Met Leu Arg Glu Gln Val Ala Gln Leu Lys Gln Lys Val Met Asn
                325                 330                 335

Tyr Ser Ser Glu Pro Lys Ser Ser Asp Lys Thr His Thr Cys Pro Pro
            340                 345                 350

Cys Pro Ala Pro Pro Ala Ala Gly Pro Ser Val Phe Leu Phe Pro Pro
        355                 360                 365

Lys Pro Lys Asp Thr Leu Met Ile Ser Arg Thr Pro Glu Val Thr Cys
    370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
                405                 410                 415

Glu Gln Tyr Asn Ser Thr Tyr Arg Val Val Ser Val Leu Thr Val Leu
            420                 425                 430

His Gln Asp Trp Leu Asn Gly Lys Glu Tyr Lys Cys Ala Val Ser Asn
        435                 440                 445

Lys Gly Leu Ala Ser Ser Ile Glu Lys Thr Ile Ser Lys Ala Lys Gly
    450                 455                 460

Gln Pro Arg Glu Pro Gln Val Tyr Thr Leu Pro Pro Ser Arg Asp Glu
465                 470                 475                 480

Leu Thr Lys Asn Gln Val Ser Leu Thr Cys Leu Val Lys Gly Phe Tyr
                485                 490                 495

Pro Ser Asp Ile Ala Val Glu Trp Glu Ser Asn Gly Gln Pro Glu Asn
            500                 505                 510

Asn Tyr Lys Thr Thr Pro Pro Val Leu Asp Ser Asp Gly Ser Phe Phe
        515                 520                 525

Leu Tyr Ser Lys Leu Thr Val Asp Lys Ser Arg Trp Gln Gln Gly Asn
    530                 535                 540

Val Phe Ser Cys Ser Val Met His Glu Ala Leu His Asn His Tyr Thr
```

```
            545                 550                 555                 560
        Gln Lys Ser Leu Ser Leu Ser Pro Gly Lys Asp Pro Gly Trp Ser His
                        565                 570                 575

Pro Gln Phe Glu Lys Ser Arg Gly Gly Gly Gln Val Gln Leu Gln
                        580                 585                 590

Gln Ser Gly Ala Glu Leu Ala Arg Pro Gly Ala Ser Val Lys Met Ser
                    595                 600                 605

Cys Lys Ala Ser Gly Tyr Thr Phe Thr Arg Tyr Thr Met His Trp Val
                    610                 615                 620

Lys Gln Arg Pro Gly Gln Gly Leu Glu Trp Ile Gly Tyr Ile Asn Pro
        625                 630                 635                 640

Ser Arg Gly Tyr Thr Asn Tyr Asn Gln Lys Phe Lys Asp Lys Ala Thr
                        645                 650                 655

Leu Thr Thr Asp Lys Ser Ser Thr Ala Tyr Met Gln Leu Ser Ser
                        660                 665                 670

Leu Thr Ser Glu Asp Ser Ala Val Tyr Tyr Cys Ala Arg Tyr Tyr Asp
                        675                 680                 685

Asp His Tyr Cys Leu Asp Tyr Trp Gly Gln Gly Thr Thr Leu Thr Val
                    690                 695                 700

Ser Gly Asn Ser Gly Gly Gly Ser Gly Gly Gly Ser Gly
        705                 710                 715                 720

Gly Gly Gly Ser Ala Ser Gln Ile Val Leu Thr Gln Ser Pro Ala Ile
                        725                 730                 735

Met Ser Ala Ser Pro Gly Glu Lys Val Thr Met Thr Cys Ser Ala Ser
                        740                 745                 750

Ser Ser Val Ser Tyr Met Asn Trp Tyr Gln Gln Lys Ser Gly Thr Ser
                        755                 760                 765

Pro Lys Arg Trp Ile Tyr Asp Thr Ser Lys Leu Ala Ser Gly Val Pro
                    770                 775                 780

Ala His Phe Arg Gly Ser Gly Ser Gly Thr Ser Tyr Ser Leu Thr Ile
        785                 790                 795                 800

Ser Gly Met Glu Ala Glu Asp Ala Ala Thr Tyr Tyr Cys Gln Gln Trp
                        805                 810                 815

Ser Ser Asn Pro Phe Thr Phe Gly Ser Gly Thr Lys Leu Glu Ile Asn
                        820                 825                 830

Gly Asn Ser
                835

<210> SEQ ID NO 51
<211> LENGTH: 834
<212> TYPE: PRT
<213> ORGANISM: Artificial Sequence
<220> FEATURE:
<223> OTHER INFORMATION: C8- hIgG1Fcmut-9.3 with Fos leucine zipper
      dimerization domain

<400> SEQUENCE: 51

Met Asp Phe Glu Val Gln Ile Phe Ser Phe Leu Leu Ile Ser Ala Ser
1               5                   10                  15

Val Ile Met Ser Arg Met Ala Glu Val Gln Leu Val Glu Ser Gly Gly
                20                  25                  30

Gly Leu Leu Gln Pro Gly Gly Ser Leu Arg Leu Ser Cys Ala Ala Ser
            35                  40                  45

Gly Phe Thr Phe Ser Gly Tyr Ala Met Ser Trp Val Arg Gln Ala Pro
        50                  55                  60
```

-continued

Gly Lys Gly Leu Glu Trp Val Ser Ser Ile Ser Gly Gly Ser
65                  70                  75                  80

Thr Tyr Tyr Ala Asp Ser Val Lys Gly Arg Phe Thr Ile Ser Arg Asp
                85                  90                  95

Asn Ser Lys Asn Thr Leu Tyr Leu Gln Met Asn Ser Leu Arg Ala Glu
            100                 105                 110

Asp Thr Ala Leu Tyr Tyr Cys Ala Lys Pro Pro Gly Arg Gln Glu Tyr
            115                 120                 125

Tyr Gly Ser Ser Ile Tyr Tyr Phe Pro Leu Gly Asn Trp Gly Gln Gly
        130                 135                 140

Thr Leu Val Thr Val Ser Ser Ala Ser Thr Lys Gly Pro Lys Leu Glu
145                 150                 155                 160

Glu Gly Glu Phe Ser Glu Ala Arg Val Gln Ser Ala Leu Thr Gln Pro
                165                 170                 175

Ala Ser Val Ser Val Ala Pro Gly Gln Thr Ala Arg Ile Thr Cys Gly
            180                 185                 190

Gly Asn Asn Ile Gly Ser Lys Ser Val His Trp Tyr Gln Gln Lys Pro
        195                 200                 205

Gly Gln Ala Pro Val Leu Val Val Tyr Asp Asp Ser Asp Arg Pro Ser
210                 215                 220

Gly Ile Pro Glu Arg Phe Ser Gly Ser Asn Ser Gly Asn Thr Ala Thr
225                 230                 235                 240

Leu Thr Ile Ser Arg Val Glu Ala Gly Asp Glu Ala Asp Tyr Tyr Cys
                245                 250                 255

Gln Val Trp Asp Ser Ser Ser Asp Leu Val Val Phe Gly Gly Gly Thr
            260                 265                 270

Lys Leu Thr Val Leu Gly Asn Ser Gly Gly Gly Gly Ser Gly Gly Gly
        275                 280                 285

Gly Ser Gly Gly Gly Gly Ser Ala Ser Leu Thr Asp Thr Leu Gln Ala
        290                 295                 300

Glu Thr Asp Gln Leu Glu Asp Lys Lys Ser Ala Leu Gln Thr Glu Ile
305                 310                 315                 320

Ala Asn Leu Leu Lys Glu Lys Glu Lys Leu Glu Phe Ile Leu Ala Ala
                325                 330                 335

Tyr Ser Ser Glu Pro Lys Ser Ser Asp Lys Thr His Thr Cys Pro Pro
            340                 345                 350

Cys Pro Ala Pro Pro Ala Ala Gly Pro Ser Val Phe Leu Phe Pro Pro
        355                 360                 365

Lys Pro Lys Asp Thr Leu Met Ile Ser Arg Thr Pro Glu Val Thr Cys
    370                 375                 380

Val Val Val Asp Val Ser His Glu Asp Pro Glu Val Lys Phe Asn Trp
385                 390                 395                 400

Tyr Val Asp Gly Val Glu Val His Asn Ala Lys Thr Lys Pro Arg Glu
                405                 410                 415

Glu Gln Tyr Asn Ser Thr Tyr Arg Val Val Ser Val Leu Thr Val Leu
            420                 425                 430

His Gln Asp Trp Leu Asn Gly Lys Glu Tyr Lys Cys Ala Val Ser Asn
        435                 440                 445

Lys Gly Leu Ala Ser Ser Ile Glu Lys Thr Ile Ser Lys Ala Lys Gly
        450                 455                 460

Gln Pro Arg Glu Pro Gln Val Tyr Thr Leu Pro Pro Ser Arg Asp Glu
465                 470                 475                 480

Leu Thr Lys Asn Gln Val Ser Leu Thr Cys Leu Val Lys Gly Phe Tyr

```
                485                 490                 495
Pro Ser Asp Ile Ala Val Glu Trp Glu Ser Asn Gly Gln Pro Glu Asn
                500                 505                 510

Asn Tyr Lys Thr Thr Pro Pro Val Leu Asp Ser Asp Gly Ser Phe Phe
            515                 520                 525

Leu Tyr Ser Lys Leu Thr Val Asp Lys Ser Arg Trp Gln Gln Gly Asn
        530                 535                 540

Val Phe Ser Cys Ser Val Met His Glu Ala Leu His Asn His Tyr Thr
545                 550                 555                 560

Gln Lys Ser Leu Ser Leu Ser Pro Gly Lys Asp Pro Gly Trp Ser His
                565                 570                 575

Pro Gln Phe Glu Lys Ser Ser Gly Gly Gly Gln Val Gln Leu Gln
                580                 585                 590

Glu Ser Gly Pro Gly Leu Val Thr Pro Ser Gln Ser Leu Ser Ile Thr
                595                 600                 605

Cys Thr Val Ser Gly Phe Ser Leu Ser Asp Tyr Gly Val His Trp Val
                610                 615                 620

Arg Gln Ser Pro Gly Gln Gly Leu Glu Trp Leu Gly Val Ile Trp Ala
625                 630                 635                 640

Gly Gly Gly Thr Asn Tyr Asn Ser Ala Leu Met Ser Arg Lys Ser Ile
                645                 650                 655

Ser Lys Asp Asn Ser Lys Ser Gln Val Phe Leu Lys Met Asn Ser Leu
                660                 665                 670

Gln Ala Asp Asp Thr Ala Val Tyr Tyr Cys Ala Arg Asp Lys Gly Tyr
                675                 680                 685

Ser Tyr Tyr Tyr Ser Met Asp Tyr Trp Gly Gln Gly Thr Thr Val Thr
                690                 695                 700

Val Ser Ser Arg Gly Gly Gly Ser Gly Gly Gly Gly Ser Gly Gly Gly
705                 710                 715                 720

Gly Ser Asp Ile Glu Leu Thr Gln Ser Pro Ala Ser Leu Ala Val Ser
                725                 730                 735

Leu Gly Gln Arg Ala Thr Ile Ser Cys Arg Ala Ser Glu Ser Val Glu
                740                 745                 750

Tyr Tyr Val Thr Ser Leu Met Gln Trp Tyr Gln Gln Lys Pro Gly Gln
                755                 760                 765

Pro Pro Lys Leu Leu Ile Phe Ala Ala Ser Asn Val Glu Ser Gly Val
                770                 775                 780

Pro Ala Arg Phe Ser Gly Ser Gly Ser Gly Thr Asn Phe Ser Leu Asn
785                 790                 795                 800

Ile His Pro Val Asp Glu Asp Val Ala Met Tyr Phe Cys Gln Gln
                805                 810                 815

Ser Arg Lys Val Pro Tyr Thr Phe Gly Gly Gly Thr Lys Leu Glu Ile
                820                 825                 830

Lys Arg
```

TRISPECIFIC BINDING MOLECULES FOR TREATING HBV INFECTION AND ASSOCIATED CONDITIONS

RELATED APPLICATIONS

This application is the National Phase of International Application No. PCT/EP2016/055717, filed Mar. 16, 2016, which designates the U.S. and that International Application was published under PCT Article 21(2) in English, which claims priority to European Application No. EP15159274.8, filed Mar. 16, 2015, all of which applications are expressly incorporated herein by reference in their entirety.

BACKGROUND OF THE INVENTION

1. Field of the Invention

The present invention relates to a binding molecule comprising at least three binding specificities, wherein (a) the first specificity is for a Hepatitis B virus (HBV) surface antigen selected from HBV small surface antigen, HBV medium surface antigen and HBV large surface antigen; (b) (i) the second and third specificity are for CD3 and CD28, respectively; or (ii) the second and third specificity are selected from specificities for CD16, CD56, NKp30, NKp46, 4-1BB and NKG2D; and (c) each binding specificity is provided by one or more binding sites, each binding site being independently provided by (i) a set of six complementarity determining regions (CDRs), wherein said set of six CDRs consists of a first set of three CDRs and a second set of three CDRs, wherein said first and said second set is each comprised in an immunoglobulin domain; or (ii) a set of three CDRs, wherein said set of three CDRs is comprised in an immunoglobulin domain.

In this specification, a number of documents including patent applications and manufacturer's manuals is cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

About 350 million humans are chronically infected with hepatitis B virus (HBV). HBV infection may entail liver cirrhosis and hepatocellular carcinoma (HCC) which cause about one million casualties per year (Ganem et al., Hepatitis B virus infection—natural history and clinical consequences. N Engl J Med; 350:1118-29 (2004)). Infections with HBV presently cannot be controlled in about 5% of adult patients and about 90% of newborns. In such a case, the HBV infection becomes chronic. The likely cause is an insufficient cellular immune response. The presently available antiviral drugs, which are used for treatment of HBV infection, inhibit viral replication. However, the covalently closed circular DNA (cccDNA) remains in the nucleus of infected hepatocytes and may cause a reactivation of the HBV infection once the patient stops to take the medication. Therefore, it would be indispensable to eliminate HBV infected cells carrying said cccDNA if the infection were to be cured completely (Protzer et al., Nat Immunol Rev 12: 2013-213 (2012)).

However, such cytotoxic elimination of HBV infected cells (be it by cytotoxic T lymphocytes or natural killer (NK) cells) does not occur or not to a sufficient degree.

Infected cells carrying a HBV cccDNA display on their surface viral surface proteins. It is presumed that this occurs although the virus is released into intracellular vesicles because a number of HBV surface proteins remain integrated into the intracellular membrane of the endoplasmic reticulum. In the course of vesicle transport processes said intracellular membrane may fuse with the cellular membrane, the consequence being that HBV surface proteins are displayed on the surface of the infected cell.

Bohne et al. (T cells redirected against hepatitis B virus surface proteins eliminate infected hepatocytes. Gastroenterology; 134:239-247 (2008)) and Krebs et al. (T Cells Expressing a Chimeric Antigen Receptor That Binds Hepatitis B Virus Envelope Proteins Control Virus Replication in Mice. Gastroenterology (2013)) describe chimeric antigen receptors which, when retrovirally delivered and expressed on the surface of a T cell, enable primary human and murine T cells to recognize hepatocytes displaying HBV small surface antigen and lyse HBV replicating cells.

EP 2 524 699 A1 describes trifunctional antibodies. These antibodies "have a functional Fc portion" and "must consist of heavy immunoglobulin chains of different subclasses". Hornig and Färber-Schwarz on the other hand describe in Chapter 40 of "Antibody Engineering" (ed. Patrick Channes, Humane Press, 2012) an scFv construct which is devoid of the Fc portion.

Liao et al. (Oncology Reports 3, 637-644 (1996)) describe bispecific monoclonal antibodies retargeting effector cells for lysis of human hepatoma xenografts in nude mice. The bispecific antibodies described are generated by the fusion of two hybridomas, resulting in a hybridoma cell line expressing the heavy/light chain combinations of two distinct antibodies. This may result in pairing of the two different heavy chains, but also in the pairing of identical heavy chains, giving rise to a random mixture of monospecific parental and bi-specific antibodies. The bispecific antibodies contain heavy and light chain and dimerize to form an Ig molecule.

In view of the prior art, the technical problem could be seen in the provision of alternative or improved means and methods of treating HBV infection as well as conditions caused by HBV infection such as liver cirrhosis or hepatocellular carcinoma. The technical problem to be solved can also be seen in the provision of a method of curing a HBV infection. Expressed in terms of cell biology, the technical problem can be seen in the provision of means and methods for the eradication of cells bearing HBV cccDNA. This technical problem is solved by the enclosed claims.

Accordingly, the present invention relates in a first aspect to a binding molecule comprising at least three binding specificities, wherein (a) the first specificity is for a Hepatitis B virus (HBV) surface antigen selected from HBV small surface antigen, HBV medium surface antigen and HBV large surface antigen; (b) (i) the second and third specificity are for CD3 and CD28, respectively; or (ii) the second and third specificity are selected from specificities for CD16, CD56, NKp30, NKp46, 4-1BB and NKG2D; and (c) each binding specificity is provided by one or more binding sites, each binding site being independently provided by (i) a set of six complementarity determining regions (CDRs), wherein said set of six CDRs consists of a first set of three CDRs and a second set of three CDRs, wherein said first and said second set is each comprised in an immunoglobulin domain; or (ii) a set of three CDRs, wherein said set of three CDRs is comprised in an immunoglobulin domain.

"HBV surface antigen" is also abbreviated "HBs" or "HBsAg".

The binding capabilities of the binding molecule according to the invention are functionally defined by using the term "binding specificity". The structural elements providing said binding specificities are referred to as "binding sites". It is envisaged with regard to each of the mentioned specificities that one or a plurality of binding sites providing a given specificity are present in the binding molecule in accordance with the present invention. To the extent a given binding specificity is implemented in the binding molecule according to the invention by means of more than one binding site, it is understood that preference is given to the binding sites implementing a given binding specificity being identical in terms of both structure and function, function being the recognition of a given epitope of the antigen to be bound. This does not exclude, though, embodiments where a given binding specificity is implemented by a plurality of binding sites which binding sites, while binding to the same antigen, do so via different epitopes of the antigen. This typically also entails structural differences between the binding sites, even though, in overall terms, they share the capability to bind to the same antigen.

Depending on the precise number, exemplary numbers being one, two, three and four, two being preferred, of binding sites providing a given specificity overall binding properties may be fine tuned or optimized. Typically, by increasing the number of binding sites providing a given specificity, binding kinetics as well as binding thermodynamics may be improved.

The total number of binding sites is also referred to as "valency" in the art. Accordingly, while there is a requirement for a binding molecule which is trispecific that it is at least trivalent, it is understood that binding molecules according to the present invention may also be tetravalent, pentavalent, hexavalent, heptavalent or octavalent. Yet higher valencies are envisaged as well. It is anticipated that the eradication of cells bearing HBV cccDNA is achieved also by using nonavalent, decavalent binding molecules or binding molecules with a yet higher number of valencies.

For the binding molecule to be at least trispecific it is sufficient that each binding specificity is represented by exactly one binding site. Accordingly, a trispecific binding molecule according to the present invention may be a trivalent molecule. Generally speaking, preference is given to those trispecific molecules, wherein one, two or three binding specificities are each implemented with two binding sites. Preference is also given to those trispecific molecules, wherein one, two or three binding specificities are each implemented with three binding sites.

It is also possible that the three binding specificities are implemented by a different number of binding sites each. It may be preferred that one binding specificity is represented by more binding sites than the other two or that two binding specificities may be represented by more binding sites than the third one.

As it is apparent from item (c)(i) of the first aspect, a set of six CDRs is a preferred implementation of a given binding site. As is well-known in the art, sets of six CDRs contain a first and a second set, each consisting of three CDRs. These two sets of three CDRs may be located on the same polypeptide chain or on different polypeptide chains, thereby giving rise to different molecular architectures. Also, it is envisaged that within a given binding molecule in accordance with the present invention, a part of the binding sites is such that all six CDRs constituting a given binding site are located on a single polypeptide chain, whereas other binding sites are such that the first and second set of three CDRs constituting a given binding site are located on distinct polypeptides. Distinct polypeptides may be merely formally distinct and otherwise identical, especially as regards the amino acid sequence. Alternatively, distinct polypeptides may be distinct from each other in terms of their amino acid sequence.

Generally speaking, and this will be also apparent from the discussion of preferred embodiments below, binding molecules according to the present invention may exclusively exhibit binding sites which are formed by one polypeptide. It is understood, though, that this does not amount to a requirement that the binding molecule as a whole consists of a single polypeptide chain. On the other hand, the present invention extends to binding molecules where all binding sites are formed by two polypeptide chains. Similarly, the latter statement does not amount to a requirement that the binding molecule as a whole consists of-only-two polypeptide chains. Instead, binding molecules may also consist of more than two polypeptide chains such as three or four or more than four polypeptide chains. Finally, as mentioned above, and as exemplified by the below structure (III), one part of the binding sites comprising a binding molecule of the present invention may be such that each of them is formed by two polypeptide chains, whereas the remainder of the binding sites is such that it is formed by a single polypeptide chain.

In relation to item (b)(ii) it is understood that second and third specificity are different from each other, thereby providing for an at least trispecific binding molecule.

To the extent item (c)(i) is considered, it follows from the requirement of six CDRs that two immunoglobulin domains are required to form a single binding site. This is different from item (c)(ii), wherein a single immunoglobulin domain is sufficient to provide a binding site, the binding site in that case consisting of three CDRs. This is also known as a single domain binding site.

The term "complementarity determining region", abbreviated as "CDR" has its meaning as established in the art. These are short subsequences, typically in the range from about 3 to about 25 amino acids, which confer to an antibody the capability to specifically recognize an epitope of an antigen. In general, the variable domain of the light chain of an antibody provides three CDRs and the variable domain of the heavy chain of an antibody provides three CDRs. If not specified differently, the six CDRs defining a binding site are normally presented in the following order: CDR1 of the heavy chain, CDR2 of the heavy chain, CDR3 of the heavy chain, CDR1 of the light chain, CDR2 of the light chain, CDR3 of the light chain. While CDRs are typically part of immunoglobulin domains, there is no requirement in that respect in accordance with the present invention. What is sufficient is an amino acid sequence, which comprises said CDRs provided that said amino acid sequence, when folded under physiological conditions, presents said CDRs in spatial proximity and maintains their capability to recognize the cognate antigen. The mentioned spatial proximity and capability of antigen binding may also be termed "configured to bind an antigen". The term "immunoglobulin domain" is known in the art and refers to a sequence of typically 70 to 100 amino acids assuming a three-dimensional structure of a 2-layer sandwich of between 7 and 9 anti-parallel β-strands. In the structures defining certain embodiments as well as in the figures, ellipses are used to depict a single immunoglobulin domain.

A set of six CDRs generally defines a binding site. In the alternative, and as known from camelid and cartilaginous fish antibodies, a set of three CDRs (CDR1, CDR2, CDR3) may define a binding site. As known in the art, and while not being required, preference is given to such sets of three CDRs wherein the CDR3 consist of a more protruding peptide loop than in naturally occurring immunoglobulin variable domains.

The term "antigen" has its art-established meaning. It refers to a molecule which is specifically recognized and bound by a set of six CDRs which typically are presented by immunoglobulin domains. The specific part of an antigen recognized and bound by said CDRs is also known as epitope.

HBV S/M/L surface proteins are the small, medium and large surface proteins in the outer envelope of HBV (Stibbe, W., and W. H. Gerlich. Structural relationships between minor and major proteins of hepatitis B surface antigen. J. Virol. 1983 46:626-628).

The three HBV surface antigens are transcribed and translated from one open reading frame and differ from each other by the length of the N-terminal part. Accordingly, the large surface antigen comprises a part which is neither present in the medium nor in the small surface antigen, and the medium surface antigen comprises a part which—while being comprised in the large antigen—is not comprised in the small antigen. The small antigen consists of a sequence, which is comprised in the C-terminal part of both the medium and the large antigen.

The large HBV surface antigen may be inserted in two manners in the cytoplasmic membrane. Either the N-terminus or the C-terminus may be located on the extracellular side. Both configurations are found in HBV infected cells. In other words, the N-terminus of the large HBV surface antigen can be located either on the cytosolic or luminal side of the ER membrane and consequently also be present in these configurations in the outer envelope of the HBV particle and the plasma membrane of the infected hepatocyte.

Surprisingly, combining second and third specificities in accordance with (b) into trispecific molecules provides for a significantly stronger activation of immune effector cells than a combination of two bispecific molecules. Reference is made to the examples.

In a further preferred embodiment, a binding site providing a binding specificity for an HBV surface antigen binds an epitope which is located (a) in said HBV small surface antigen; or (b) in the part of said HBV large surface antigen which is not comprised by said HBV small surface antigen; or (c) in a part of said HBV large surface antigen which part varies in structure from said HBV small surface antigen.

Item (a) refers to epitopes present in the HBV small surface antigen. Owing to the above described relation between small, medium and large HBV surface antigen, the entire sequence of the small antigen is comprised in the medium and the large antigen. In general, but not necessarily, a three-dimensional epitope presented by the small surface antigen will also be presented by the medium and/or the large surface antigen.

In accordance with item (b) it is preferred that said part of said HBV large surface antigen is also not comprised by said HBV medium surface antigen. As regards item (c), it is understood that "varying in structure" includes epitopes of said HBV large surface antigen which comprise or consist of sequences which are part of the sequence of said HBV small surface antigen, wherein said epitopes are not present on said HBV small surface antigen. In accordance with item (c) it is furthermore preferred that said epitope is in a part of said HBV large surface antigen which part varies in structure also from said HBV medium surface antigen.

Said item (a), i.e. said first antigen being said HBV small surface antigen is particularly preferred in conjunction with all aspects and embodiments of this invention.

In accordance with items (b) and (c), the polypeptide or binding molecule, respectively, will specifically recognize the large surface antigen of HBV.

Second and third specificities are directed to surface antigens presented by immune effector cells, preferably specifically presented by NK cells and/or CTLs. Immune effector cells are the cells to be redirected to HBV infected cells, said HBV infected cells presenting the mentioned HBV surface antigens on their surface.

It is particularly preferred that second and third specificity are either both for CTLs or both for NK cells.

CD3 (cluster of differentiation 3) T-cell co-receptor is a protein complex and is composed of four distinct chains. In mammals, the complex contains a CD3γ chain, a CD3δ chain, and two CD3ε chains. Binding specificities may be directed to any of these chains. These chains associate with a molecule known as the T-cell receptor (TCR) and the ζ-chain to generate an activation signal in T lymphocytes. The TCR, ζ-chain, and CD3 molecules together comprise the TCR complex.

In a preferred embodiment, CD3 stands for the CD3 epsilon chain, which is part of the CD3-T-cell receptor complex. (Borst, J. et al., The delta- and epsilon-chains of the human T3/T-cell receptor complex are distinct polypeptides. Nature. 1984. 312: 455-458). Preferably, the binding specificity for CD3 in accordance with the invention is for said CD3 epsilon chain.

CD28 is a major T cell costimulatory receptor. (Lesslauer, W. et al., T90/44 (9.3 antigen). A cell surface molecule with a function in human T cell activation. Eur. J. Immunol. 1986. 16: 1289-1296).

4-1BB (CD137) is a costimulatory receptor of activated T cells and NK cells. (Kwon, B. S. et al., cDNA sequences of two inducible T-cell genes. Proc. Natl. Acad. Sci. U.S.A. 1989. 86:1963-1967).

CD16 (FcγRIIIa) is a low affinity Fc receptor expressed by NK cells, a subset of activated cytotoxic T cells as well by cell types from the myelomonocytic lineage, binding to the Fc domain of IgG molecules. (Lanier, L. L. et al., Functional properties of a unique subset of cytotoxic CD3+ T lymphocytes that express Fc receptors for IgG (CD16/Leu-11 antigen). J. Exp. Med. 1985. 162: 2089-2106).

CD56 (NCAM) is a cell adhesion molecule expressed by NK cells. (Lanier, L. L. et al., Identity of Leu-19 (CD56) leukocyte differentiation antigen and neural cell adhesion molecule. J. Exp. Med. 1989. 169: 2233-2238).

NKG2D is an activating receptor expressed by NK cells (Houchins, J. et al., DNA sequence analysis of NKG2, a family of related cDNA clones encoding type II integral membrane proteins on human natural killer cells. 1991. J. Exp. Med. 173: 1017-1020).

NKp30 (NCR3) is an activating receptor expressed by NK cells (Pende, D. et al., Identification and molecular characterization of NKp30, a novel triggering receptor involved in natural cytotoxicity mediated by human natural killer cells. 2000. J. Exp. Med. 192: 337-346).

NKp46 (NCR1) is an activating receptor expressed by NK cells (Pessino et al., Molecular cloning of NKp46: a novel member of the immunoglobulin superfamily involved in triggering of natural cytotoxicity. 1998. J. Exp. Med. 188: 953-960).

CD3, CD28 and 4-1BB are present on the surface of CTLs. Binding of a polypeptide of the invention to any of these surface antigen entails stimulation or co-stimulation of CTLs.

CD16, CD56, NKG2D, NKp30, NKp46 and 4-1BB are present on the surface of NK cells. Binding of a polypeptide of the invention to any of these surface antigens entails stimulation or co-stimulation of NK cells.

With regard to human CTLs, preference is given to CD3 and CD28. With regard to human NK cells, preference is given to CD16 and CD56.

The mentioned surface antigens are designated by art-established names, (see also Kenneth Murphy, Janeway's Immunobiology, 7$^{th}$ edition, Garland Science; William E. Paul, Fundamental Immunology, 7$^{th}$ edition, Lippincott Williams & Wilkins).

It is particularly preferred that binding in accordance with the invention, in particular between CDRs and antigens is specific. The terms "specifically binds" and "specifically binding" (having the same meaning as "specifically interacting") as used in accordance with the present invention mean that these binding portions do not or essentially do not cross-react with an epitope or a structure similar to that of the target antigen. Cross-reactivity of a panel of molecules under investigation may be tested, for example, by assessing binding of said panel of molecules under conventional conditions to the epitope of interest as well as to a number of more or less (structurally and/or functionally) closely related epitopes. Only those molecules that bind to the epitope of interest in its relevant context (e.g. a specific motif in the structure of a protein) but do not or do not essentially bind to any of the other epitopes are considered specific for the epitope of interest.

Chronic HBV infection is characterized by an immuno-tolerant status. More specifically, the patient's CTLs and NK cells perform such that a complete eradication of infected cells or a complete control of HBV replication or a complete elimination of HBV does not occur. The binding molecules according to the invention specifically recognize a HBV surface antigen on the one hand and an immune effector cell surface antigen on the other hand. The binding molecules of the invention could be seen as conferring an artificial specificity to immune effector cells. In fact, CTLs and NK cells are retargeted by the binding molecules of the invention such that they are recruited to HBV infected cells and kill them.

Binding of the binding molecules of the invention to HBV infected cells on the one hand and recruiting of immune effector cells on the other hand may occur in any order or also simultaneously.

In particular, it is intended to systemically apply binding molecules of the invention by either injection or as an oral application form and allow them to bind to HBV-infected or HBV antigen expressing target cells and recruit said immune effector cells to said target cells.

Having said that, it is also envisaged to bring binding molecules of the invention into contact with immune effector cells (or a population of peripheral blood mononuclear cells comprising said effector cells) such that said effector cells get loaded with said binding molecules. Such effector cells which have been loaded in vitro or ex vivo (or a population of PBMCs comprising such loaded effector cells) may then be administered to a patient suffering from HBV infection or a condition associated therewith and defined below. Such administering may be effected intravascularly, e.g. to the *Arteria hepatica*. An immune effector cell with a binding molecule according to the present invention being bound to a surface antigen of said immune effector cell is also an aspect of the present invention. This aspect is disclosed further below.

This killing, in particular in conjunction with antiviral immune mediators (e.g. cytokines) as secreted by immune cells, provide for the eradication of HBV infection or for the sustained control of HBV infection or for the elimination of tumor cells expressing HBV surface antigens.

Preferred measures of performance of the binding molecules of the invention include T-cell mediated cytotoxicity in cell culture, recruiting of T-cells into the liver, inflammatory response of the liver, decrease of viral titers in serum, decrease of the viral antigens HBsAg and/or HBeAg in serum, decrease of viral replication in the liver, and decrease of the number of infected cells.

Each of these properties can be measured by art-established procedures.

To explain further, recruiting of T-cells to the liver may be quantified by determining levels of one or more T-cell marker gene mRNAs, in particular of CD3, CD4, CD8, IFNγ and IP-10 (CXCL10) via RT-PCR in the liver. According to the present invention, the induction of these marker genes is significantly induced in comparison to a negative control and may reach levels of 2-fold to 1000-fold induction or above, preferably more than 2-fold, preferably more than 5-fold, preferably more than 10-fold, preferably more than 25-fold, preferably more than 50-fold, preferably more than 100-fold, preferably more than 500-fold, preferably more than 750-fold, preferably more than 1000-fold.

According to the present invention, T-cell mediated cytotoxicity in cell culture is in the range of 5% to 100%, preferably more than 5%, preferably more than 10%, preferably more than 20%, preferably more than 30%, preferably more than 40%, preferably more than 50%, preferably more than 75%, preferably 100%.

T-cell mediated cytotoxicity in vivo can be assessed, for example, by measurement of liver transaminases (preferably alanine transaminase (ALT) and/or aspartate transaminase (AST)) which are released by eliminated hepatocytes. Normal ALT levels in individuals are below 40 international units per liter (U/l) and can reach levels of 50 U/l to 5000 U/l upon efficient cytotoxicity by retargeting of immune effector cells. Preferably, levels will be more than 50 U/l, preferably more than 100 U/l, preferably more than 200 U/l, preferably more than 300 U/l, preferably more than 400 U/l, preferably more than 500 U/l, preferably more than 750 U/l, preferably more than 1000 U/l.

According to the present invention, inflammatory responses of the liver may be determined by means of HE staining. HE stands for Hematoxilin and Eosin and is the standard staining technique for pathology and allows for visualization of cellular structures in shades of blue, purple, red pink and orange. With this method infiltrating immune effector cells can be visualized and quantified in comparison to a negative control and numbers will increase according to the present invention in a range of 5-fold to 5000-fold in comparison to an untreated control, preferably more than 5-fold, preferably more than 10-fold, preferably more than 20-fold, preferably more than 50-fold, preferably more than 100-fold, preferably more than 250-fold, preferably more than 500-fold, preferably more than 1000-fold.

CD3 staining of biopsies taken from the liver and/or staining for trispecific binding molecules of the invention reveals the specific infiltration of T cells and redirected T cells respectively. With this method redirected CD3+ T cells can be visualized and quantified in comparison to a negative control and numbers will increase according to the present invention in a range of 5-fold to 5000-fold in comparison to an untreated control, preferably more than 5-fold, preferably more than 10-fold, preferably more than 20-fold, preferably more than 50-fold, preferably more than 100-fold, preferably more than 250-fold, preferably more than 500-fold, preferably more than 1000-fold.

Virus replication may be quantified by using PCR and/or Southern blotting on serum or liver tissue samples. The application of the binding molecule of the invention to an HBV infected subject causes a decrease of viral titers in serum. According to the present invention it is envisaged that a decrease of more than 10%, preferably more than 20%, preferably more than 30%, preferably more than 40%, preferably more than 50%, preferably more than 60%, preferably more than 70%, preferably more than 80%, preferably more than 90%, preferably below the level of detection (50 HBV DNA copies per ml) of viral titers in serum is achieved after application of the effective amount of the binding molecule. E.g. serum HBV DNA reaches levels of up to $10^9$ copies per ml in HBV-transgenic mice and can be reduced to $10^7$ copies/ml upon treatment with redirected T cells (Krebs et al. T Cells Expressing a Chimeric Antigen Receptor That Binds Hepatitis B Virus Envelope Proteins Control Virus Replication in Mice. Gastroenterology (2013)).

The number of still infected cells may be determined by staining liver slices for HBeAg, HBcAg or HBsAg. In comparison to untreated controls, the reduction in HBV-replicating cells according to the present invention will range from a minimum of 5% to maximally 100%, preferably more than 5%, preferably more than 10%, preferably more than 20%, preferably more than 30%, preferably more than 50%, preferably more than 70%, preferably more than 90%, preferably 100%.

"Viral titer" (also known as viral load, viral burden) is a term well-known in the art, indicating the amount of virus in a given biological sample. Amount of virus are indicated by various measurements, including, but not limited to, amount of viral nucleic acid; presence of viral (such as complete virions, determined by sedimentation gradient centrifugation) and subviral particles (such as HBsAg or hepatitis B surface antigen particles, determined by immunoassays such as ELISA). Generally, for fluid samples such as blood and urine, amount of virus is determined per unit fluid, such as milliliters. For solid samples such as tissue samples, amount of virus is determined per weight unit, such as grams. Methods for determining amount of virus are known in the art. Currently, routine testing is e.g. available for hepatitis B virus such as viral load, qualitative and quantitative HBsAg and HBeAg measurement.

"Effective amount" refers to that amount of an agent sufficient to achieve the above-described purpose. Specifically, the amount of binding molecule according to the invention is effective in reducing viral titer levels in a hepatitis B virus-infected subject to be treated. An effective amount can be administered in one or more administrations. The effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art.

There are e.g. many different molecular based test methods for quantifying the viral load using Nucleic Acid Testing (NAT). The starting material for amplification can be used to divide these molecular methods into groups. The Polymerase Chain Reaction (PCR) method of in vitro DNA synthesis uses a DNA template, polymerase, buffers, primers, and nucleotides to multiply the HIV in the blood sample. Then a chemical reaction marks the virus. The markers are measured and used to calculate the amount of virus. PCR is used to quantify integrated DNA.

Reverse Transcription Polymerase Chain Reaction (RT-PCR) is a variation of PCR that can be used to quantify viral transcript. RNA is used as the starting material for this method and converted to double-stranded DNA, using the enzyme reverse transcriptase (RT).

Therapeutic goal of chronic hepatitis B is a "functional" cure of HBV infection, which is not achieved with currently available antiviral agents. As noted further above, major obstacles to a functional cure are intricate stability of HBV cccDNA and dysfunctional anti-HBV immune response. Functional cure of HBV in the context with the present invention means that the number of HBV genomes per ml is below 100000, preferably below 10000, more preferably below 1000, 100 or 10. Especially preferred is complete eradication or reduction below the limit of detection.

Given that binding molecules according to the present invention provide tailored specificities to immune effector cells, the naturally inherent specificity of the immune effector cells or the presentation of antigens to them becomes irrelevant. As such, a large pool of candidate effector cells is amenable to retargeting. Furthermore, the binding molecules of the invention have a bioavailability and half-life which is at least comparable to that of monoclonal antibodies.

In a preferred embodiment of the first aspect, said at least three binding specificities are (a) three specificities; or (b) four specificities, and wherein the fourth specificity is for hepatic cells.

Preference is given to the binding molecule being a trispecific binding molecule. In other words, exactly three binding specificities are present. The alternative of having a fourth specificity present may be advantageous for targeting to certain cells, in particular to hepatic cells. In that respect, a preferred marker on hepatic cells is NTCP. NTCP is known in the art as the HBV entry-mediating receptor.

In a further preferred embodiment, said molecule is (a) a multimer of polypeptides; or (b) a polypeptide. It is understood that item (b) of this preferred embodiment defines a binding molecule which consists of a single polypeptide.

The term "polypeptide" defines a molecule which is a polycondensate of amino acids which form one single chain with one N-terminus and one C-terminus. The constituent amino acids include the 20 naturally occurring proteinogenic amino acids. Preferably, said polypeptide consists exclusively of said naturally occurring proteinogenic amino acids. Having said that, the term extends to molecules which, in addition to said naturally occurring proteinogenic amino acids, contain up to 20%, 10%, 5%, 2%, or 1% amino acids which are selected from non-naturally occurring α-amino acids, β-amino acids, D-amino acids, selenocysteine, selenomethionine, hydroxyproline, pyrrolysine and ornithine. It is furthermore understood that one or more such as 2, 3, 4, 5, 6, 7, 8, 9 or 10 amino acids may be phosphorylated. The latter applies in particular to serine, threonine and tyrosine. Also other post-translational modifications as known in the art may be present including glycosylation. Glycosylations include N-linked glycosylations, typically at an asparagine and O-linked glycosylations, typically at serine or threonine residues. N- and/or C-terminus may be protected, protection groups including acetyl for the N-terminus and amine for the C-terminus. The type of linkage between the amino acids comprised in said polypeptide is confined to amide (CONH) bonds. The term "amide bond" includes peptide bonds which connect the α-carboxylate of a given amino acid to the α-amino group of the subsequent amino acid. The "amide bond" also extends to isopeptide bonds which is an amide bond that is not present on the main chain of the polypeptide. For example, instead of an α-amino group, the side chain amino group of lysine may be involved. Similarly, instead of the α-carboxyl group, the side chain carboxylate of glutamate or aspartate may be involved. The occurrence of one or more such as 2, 3, 4, 5, 6, 7, 8, 9 or 10 isopeptide bonds is envisaged. Preference is given, though, to polypeptides wherein the constituent amino acids are linked to each other exclusively by peptide bonds.

In general, there is no upper limit on the number of amino acids in a polypeptide. As can be seen from the exemplary polypeptide sequences comprised in the sequence listing, the polypeptides of the present invention typically contain several hundred amino acids, preferably between 250 and 1000, 400 and 900, or between 700 and 800 amino acids. It is common to distinguish between peptides on the one hand and polypeptide on the other hand, wherein peptides have 30 or less amino acids and polypeptides have more than 30 amino acids.

The term "multimer" according to the present invention includes dimers, trimers, tetramers, pentamers, hexamers, heptamers and octamers.

In the broadest form, there is no limitation as regards the location of the at least three required specificities on the respective constituent polypeptides of a multimer. While it is conceivable that constituent polypeptides are used, wherein each polypeptide provides exactly one binding specificity— implemented by one, two, three, four or more binding sites—preference is given to multimers, wherein each of the constituent polypeptides carries two or three specificities, constituent polypeptides with two specificities being especially preferred.

To the extent the binding molecule of the present invention, which preferably is a trispecific binding molecule, is a multimer of polypeptides, preferably a dimer or tetramer, it is preferred that (a) each polypeptide is a bispecific polypeptide; or (b) each polypeptide is independently selected from monospecific, bispecific and trispecific polypeptides.

It goes without saying that this preferred embodiment only embraces constructs which also meet the terms of the broadest definition of the first aspect of the present invention. For example, a dimer of two monospecific polypeptides would not meet the requirement "trispecific" and is therefore not embraced by this preferred embodiment.

In line with the above explained distinction between binding specificity on the one hand and binding site on the other hand, it is understood that a monospecific polypeptide may be monovalent, bivalent, trivalent, tetravalent or may contain even more than four valencies. Similarly, bispecific polypeptides may be bivalent, trivalent, tetravalent or contain more than four valencies. Finally, trispecific polypeptides may be trivalent, tetravalent or contain more than four valencies. As noted above, a binding site may be provided by two immunoglobulin domains located on the same polypeptide, but also by two immunoglobulin domains located on different polypeptides. Therefore, in those cases where the binding molecule according to the present invention is a multimer of polypeptides, the number of valencies of the binding molecule may exceed the number of valencies of all constituent polypeptides taken together. The difference between the total number of valencies in the binding molecule and the cumulative number of valencies provided by all constituent polypeptides is the number of those binding sites which are formed by two immunoglobulin domains located on distinct polypeptide chains.

Using structure (III) as disclosed further below as an example, the total number of binding sites in this molecule is five, four of which are formed by pairs of immunoglobulin domains, wherein each pair is located on a single polypeptide chain, and one binding site is formed a pair of immunoglobulin domains located on distinct polypeptide chains. The total number of polypeptides in structure (III) is two.

In terms of mechanisms of multimerization or oligomerization, it is noted that polypeptides may be linked together covalently and/or non-covalently. For example, if the binding molecule is a dimer of two polypeptides, said polypeptides may exclusively be linked together by one or more covalent bonds, said covalent bonds preferably being disulfide bonds. Alternatively, the two polypeptides may be exclusively connected by non-covalent interactions. Equally conceivable is that the two polypeptides are bound to each other by both covalent and non-covalent interactions. Similarly, and considering higher order multimers, it is understood that only covalent interactions may hold the multimer together, only non-covalent interactions, or a combination of covalent and non-covalent interactions. Combinations of covalent and non-covalent interactions may be such that for a given binary interaction within the multimer, there is only a covalent or only a non-covalent interaction, or a combination of both covalent and non-covalent interactions.

The terms "multimerization" and "oligomerization" (used equivalently) include dimerization.

As will be further detailed below, in certain instances, and for certain preferred binding molecules of the present invention, there may be a preference for covalent interaction over non-covalent interaction or vice versa.

To the extent the invention relates to multimers, constituent polypeptides further comprise a dimerization or multimerization region. Said dimerization or multimerization region may provide for covalent and/or non-covalent dimerization or multimerization.

In a particularly preferred embodiment, said dimerization region that connects two polypeptides of the invention consists of the hinge region of the IgG heavy chain or comprises the cysteine residues responsible for the dimerization of the heavy chains of an antibody. Further naturally occurring disulfide bonds which may be exploited for dimerization and multimerization are those between the respective C-terminal of the first constant domain of the heavy chain and the constant domain of the light chain.

Preferably, said dimerization region consists of a subsequence of 32 amino acids in length, the so called hinge region of the heavy chain (EPKSSDKTHTCPPCPAPEFE-GAPSVFLFPPKP, see SEQ ID NOs: 43 to 46) and comprises the two cysteine residues (underlined in above sequence) responsible for the dimerization of the heavy chains. Preferably the single cysteine residue within the hinge region of the IgG heavy chain that mediates the intermolecular disulfide bond between the IgG heavy and light chain constant domains in a natural antibody is mutated into a serine in order to prevent aberrant disulfide bridges.

Dimerization domains suitable for non-covalent dimerization are known in the art and include leucine zippers.(see, e.g., de Kruif and Logtenberg, Leucine zipper dimerized bivalent and bispecific scFv antibodies from a semi-synthetic antibody phage display library. J. Biol. Chem. 1996. 271: 7630-7634). A further option for triggering dimerization are the naturally occurring interactions between immunoglobulin domains. These interactions occur, for example, in an IgG molecule between the variable domains of heavy and light chain, between the first constant domain of the heavy chain and the constant domain of the light chain, the respective second constant domains of the heavy chains and the respective third constant domains of the heavy chains.

In a further preferred embodiment, a constituent polypeptide further comprises a spacer region, said spacer region preferably comprising a CH2 domain and a CH3 domain. In case of a constituent polypeptide comprising scFv fragments, said spacer region may be located between the first scFv fragment and the second scFv fragment.

A spacer region comprising or consisting of a CH2 domain and a CH3 domain, in particular from IgG, is advantageous. Advantages include efficient secretion from produced cells. Moreover, the capability of such spacer region to bind protein A provides a means for subsequent purification from the reagents.

Both said CH2 and CH3 domain on the one hand and said dimerization region on the other hand may be provided by the corresponding region of an IgG, preferably IgG1 or IgG2 molecule, even more preferred a human IgG1 or IgG2 (hIgG1, hIgG2) molecule. A preferred subsequence of a hIgG1 molecule providing CH2 domain and CH3 domain can be seen in SEQ ID NOs: 43 to 46. The sequences of SEQ ID NOs: 50 and 51 implement the preferred embodiment of non-covalent dimerization, more specifically via leucine zipper domains. Preferably—and this applies to the mentioned sequences—the portion of hIgG1, in particular said CH2 domain, was mutagenized in multiple positions to reduce the binding to Fc receptors (indicated in bold-face italics in the sequences given further below). More generally, the Fc region, in particular the CH2 domain and/or the CH3 domain may be mutated in one or more positions to reduce the binding to Fc receptors. Such procedure is known in the art and described, for example, in Armour et al., Recombinant human IgG molecules lacking Fc gamma receptor I binding and monocyte triggering activities. Eur. J. Immunol. 1999. 29: 2613-2624 and Shields et al., High resolution mapping of the binding site on human IgG1 for Fc gamma RI, Fc gamma RII, Fc gamma RIII, and FcRn and design of IgG1 variants with improved binding to the Fc gamma R. J. Biol. Chem. 2001. 276: 6591-6604.). This is advantageous because triggering of antibody dependent cell-mediated cytotoxicity (ADCC) is not preferred in accordance with the invention.

In other words, an antibody Fc fragment, preferably modified as defined above, may be used to implement spacer region and dimerization region. The term "Fc fragment" is known to the skilled person and defines a fragment of IgG which is obtained by cleavage with papain and comprises CH2 and CH3 domains.

Between said first scFv fragment and said spacer region and/or between said spacer region and said second scFv fragment (a) linker sequence(s) may be present. Preferred linker sequences are disclosed herein above. As can be seen from the preferred sequences comprised in the sequence listing, in particular sequences of SEQ ID NOs: 43 to 46, such linker sequences may consist of glycines or glycines and serines.

The terms "CH2 domain" and "CH3 domain" have its art-established meaning. They refer to the second and third constant domain of antibody heavy chains.

Turning to the preferred molecular architectures as displayed in the attached FIGS. 1 and 2, dimerization and multimerization, respectively, preferably occur as follows. Homodimerization of identical polypeptide chains such as in formats B, D, G, H, L, M and O is preferably effected via the formation of intermolecular disulfide bonds of the hinge domain of human IgG1. The same applies to heterodimerization of polypeptide chains of different amino acid sequences as in format C. In formats B and C, CH2 and CH3 domains contribute via non-covalent interactions to the stability of the dimer. In formats, G, H, N and O the naturally occurring intermolecular disulfide bridge between the $C_K$ and the CH1 domain contribute as a covalent mechanism to dimerization as does the non-covalent interaction between CH2 and CH3 domains. The former of these two mechanisms contributes also to dimerization and formats D, L and M.

For the purpose of heterodimerization of polypeptides with different amino acid sequences such as in formats A, E, F and K, preference is given to the above mentioned leucine zipper domains, also known as amphipathic coiled-coil dimerization domains. Examples for such dimerization domains are described in deKruif and Logtenberg, J. Biol. Chem. 271, 7630-7634 (1996) and Arndt et al., J. Mol. Biol. 312, 221-228 (2001). In formats A and E, CH2 and CH3 domains contribute to dimerization. In format F, the intermolecular disulfide bridge between $C_K$ and CH1 domain as well as the non-covalent interaction between CH2 and CH3 domains of human IgG1 contribute to dimerization.

In a further preferred embodiment, one, more or all of said polypeptides consist of or comprise one or more scFv molecules. This embodiment extends to tandem scFv molecules, also designated (scFv)$_2$ as well as to (scFv)$_3$ molecules such as structure (VII).

This preferred embodiment defines preferred constituent elements of the polypeptides comprised in binding molecules of the present invention. Polypeptides may either consist of or comprise those preferred constituent molecules. For example, when a polypeptide shall be used to provide a single binding specificity, this may be accomplished by using a polypeptide consisting of an scFv molecule. On the other hand, when use shall be made of a polypeptide providing two binding specificities, this may be accomplished by a polypeptide comprising two scFv molecules or by a diabody.

The term "scFv" is well-established in the art. The abbreviation stands for "single chain variable fragment" of an antibody and defines a polypeptide capable of specifically recognizing and binding the epitope of an antigen. As noted above, three CDRs are presented by the variable domain of an antibody light chain (VL) and three CDRs are presented by the variable domain of a heavy chain (VH) of an antibody. To the extent VL and VH are not covalently linked, they constitute an Fv fragment. In an scFv on the other hand, two variable domains are connected to each other by a peptide linker. The obtained fusion construct is a single polypeptide chain. This provides for easy expression of the scFv molecule.

The terms "VH domain" and "VL domain" are art-established. Thus, they refer to the variable region of the heavy chain (VH) and the variable region of the light chain (VL) of immunoglobulins, respectively. Generally, VH and VL domains comprise three complementarity determining regions (CDRs) each.

The terms "diabody", "triabody" and "tetrabody" are known in the art and relate to single chain constructs which contain two, three or four Fv fragments. Generally speaking, diabodies, triabodies and tetrabodies comprise two, three or four polypeptide chains. These may be linked to each other such that a single polypeptide chain is obtained. An overview of recombinant antibody constructs is Little et al., Immunology Today, 21, 364-370 (2000).

A peptide linker is preferably used to link either variable regions of an scFv or to link an scFv to a dimerization/ multimerization and/or spacer region or to an Fc as defined below. Similarly, short peptide linkers may be used in the construction of diabodies, triabodies and tetrabodies as illustrated in the above mentioned review.

Typically the peptide linkers have a length between 3 and 30 amino acids, preferably between 5 and 25 or 10 and 20 amino acids. Preference is given to those linkers, which do not or not substantially interfere with structure and or function of the domains or polypeptides they connect (connecting yields a single continuous polypeptide chain). Linkers include Gly-rich linkers such as the (Gly4Ser)3 (SEQ ID NO: 47) linker which is used in the preferred polypeptides of the invention for connecting the VH/VL domains of CTL or NK specific scFvs, and the Yol linker (SEQ ID NO: 48; AKTTPKLEEGEFSEARV, as described in Sellrie et al., Journal of Biochemistry and Molecular Biology, Vol. 40, No. 6, November 2007, pp. 875-880) which is used in the preferred polypeptides of the invention for connecting the VH/VL domains of the scFvs specific for HBV surface antigens. Also the (Gly4Ser)4 linker (SEQ ID NO: 49) may be used for connecting the VH/VL domains of the scFvs specific for HBV surface antigens or other building blocks of the binding molecules of the invention.

In a further preferred embodiment relating to those binding molecules which are multimers of polypeptides, said multimers being preferably dimers or tetramers, said binding molecule being preferably a trispecific binding molecule, one, more or all binding sites is/are provided by two of said polypeptides together.

The structural background for this preferred embodiment has been explained above. In particular, this preferred embodiment provides for the two immunoglobulin domains providing the two sets of three CDRs making up a binding site being located on distinct polypeptide chains.

In a particularly preferred embodiment, said binding molecule comprises an Fv fragment; a Fab fragment; a diabody; a triabody; a tetrabody; or an immunoglobulin G molecule, optionally with a modified Fc portion.

The terms used in relation to this particularly preferred embodiment have their art-established meaning. In particular, the term "Fv fragment" designates a non-covalent complex of two immunoglobulin domains, said immunoglobulin domains being a variable domain of a light chain and a variable domain of a heavy chain.

From a structural point of view, an Fv fragment is comprised in a Fab fragment, wherein the Fab fragment furthermore comprises the constant domain of the light chain CL and the first constant domain of the heavy chain CH1 of an antibody. Altogether, a Fab fragment comprises four immunoglobulin domains, wherein two of said four immunoglobulin domains, namely the VL and the VH domain, form together a binding site. Fab fragments may be obtained from an antibody by cleavage with the enzyme papain.

When a binding molecule according to the invention comprises an Fv fragment at a certain location, it is understood that at this particular location it has no adjacent constant domain of a light chain and no adjacent constant domain 1 of a heavy chain, noting that otherwise there would be a Fab fragment at the location under consideration. Similarly, a requirement for a Fab fragment excludes presence of CH2 and CH3 domain at the location under consideration. "Adjacent" in this context refers to a proximity as found in naturally occurring antibodies.

Modifications in the Fc portion of the recited immunoglobulin G molecule include modifications which diminish or abolish the binding to Fc receptors; see below.

There is a preference for binding molecules according to the present invention which are entirely devoid of Fc portions. Also preferred is the presence of Fc portions, wherein said Fc portions are modified as described above, or, in addition, modified so that the Fc portion is not N-glycosylated. Finally, also native Fc portions may be used.

A modification which provides for decreasing Fc binding and/or decreasing complement activation is a replacement of hIgG1-derived Fc with Fc from hIgG2 or hIgG4.

The term "antibody" as used herein has its art-established meaning. Preferably, it refers to the monoclonal antibody. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof directed to the aforementioned HBV surface proteins can be obtained by using methods which are described, e.g., in Harlow and Lane "Antibodies, A Laboratory Manual", CSH Press, Cold Spring Harbor, 1988. The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA or polypeptide sequence underlying the amino acid sequence of an immunoglobulin chain are well known to the person skilled in the art; see, e.g., Sambrook, Molecular Cloning: A Laboratory Manual, Cold Spring Harbor Laboratory, Cold Spring Harbor, N.Y., 1989. Modifications of the polypeptides include also post-translational modifications such as glycosylations.

In a preferred embodiment relating to those binding molecules of the present invention which are multimers of polypeptides and wherein each polypeptide is a bispecific polypeptide, the first specificity of each bispecific polypeptide is a first specificity as defined in accordance with the first aspect and the second specificity of each polypeptide is either for CD3 or for CD28.

Accordingly, it is understood that preference is given to constituent bispecific polypeptides which share the ability to bind a HBV surface antigen and which differ from each other with regard to their specificity for a CTL surface marker.

Especially preferred binding molecules in this regard are dimers and tetramers of polypeptides. Within that group of dimers which consists of dimers of bispecific bivalent polypeptides, preference is given to non-covalent dimers.

Especially preferred dimers are those of structures (I), (II) and (III), and an especially preferred tetramer is that of structure (IV):

"Chain A" and "Chain B" designate polypeptides with distinct amino acid sequences. "Chain A" and "Chain A'" designate distinct polypeptides with identical amino acid sequences. Specificities are indicated close to each binding site. As is common in the art, the term "anti" is abbreviated as "α".

Structure (I) is a non-covalent dimer consisting of two bispecific bivalent polypeptides. Structure (I) is illustrated in FIG. 1, "Format A".

Structure (II) is a covalent dimer of two polypeptides, wherein the polypeptide designated "Chain A" is a bispecific bivalent polypeptide, and the polypeptide designated "Chain B" is a bispecific trivalent polypeptide. Structure (II) is illustrated in FIG. 1, "Format C".

We note that structure (III) has four binding sites which each are provided by two immunoglobulin domains, said two immunoglobulin domains being located on the same polypeptide chain, and a fifth binding site which is formed by two immunoglobulin domains being located on distinct polypeptide chains. The examples include data for a structure (III) binding molecule of the invention.

Structure (IV) is illustrated in FIG. 1, "Format D". The examples include data for a structure (IV) binding molecule of the invention.

In a further preferred embodiment of the binding molecule of the present invention, said binding molecule preferably being a trispecific binding molecule, each polypeptide is a trispecific binding molecule.

In other words, each constituent polypeptide already comprises the three specificities in accordance with the first aspect of the present invention. Using a multimer of trispecific polypeptides, preferably a dimer, binding properties may be fine-tuned or optimized.

Especially preferred in this regard is a dimer of identical polypeptides, which most preferably has structure (V):

Structure (V) is illustrated in FIG. 1, "Format B".

The present invention also provides binding molecules wherein binding sites are exclusively formed by immunoglobulin domains located on distinct polypeptide chains. An example is the binding molecule having structure (VI):

Structure (VI) is a triabody. Structure (VI) is illustrated in FIG. 2, "Format J".

To provide the functionality of the binding molecule having structure (VI), also a different topology may be employed. Accordingly, the present invention in a further preferred embodiment extends to binding molecules having structure (VII):

Structure (VII) consists of one polypeptide. It implements the above disclosed (scFv)3 architecture. Structure (VII) is illustrated in FIG. 2, "Format I".

Preferred implementations of the present invention are depicted in FIG. 1. Antigens are indicated for illustration purposes. It is understood that the antigens are not part of the binding molecules according to the present invention. Further molecular architectures in accordance with the present invention are shown in FIG. 2.

The above mentioned first specificity is preferably provided by a set of six CDRs, which set of six CDRs is preferably that of SEQ ID NOs: 1 to 6, 7 to 12 or 13 to 18.

The above defined second specificity of the binding molecules of the invention directed to CD3 is preferably provided by a set of six CDRs having the sequences of SEQ ID NOs: 19 to 24.

The above defined third specificity of the binding molecules of the invention directed to CD28 is preferably provided by a set of six CDRs having the sequences of SEQ ID NOs: 25 to 30.

To the extent second and third specificities are selected from specificities for CD16, CD56, NKp30, NKp46, 4-1BB and NKG2D, preference is given to the second specificity being for CD16 and the third specificity being for CD56. Preferred corresponding sets of six CDRs are those of SEQ ID NOs: 31 to 36 and 37 to 42, respectively.

C8, 5F9, 5A19, OKT3, 9.3, A9 and NCAM29.2 as used in the sequence listing designate the antibody from which the respective CDRs originate from and refer to a preferred anti-HBs antibody, to a second different anti-HBs antibody, an antibody against HBV large surface antigen, an antibody against human CD3, an antibody against human CD28, an antibody against human CD16, and an antibody against human CD56, respectively. "HBs" designates the HBV small surface antigen.

To the extent use is made of bispecific bivalent polypeptides, it is particularly preferred that said polypeptide comprises or consists of the amino acid sequence of any one of SEQ ID NOs: 43 to 46 or an amino acid sequence which exhibits at least 80% identity to any one of SEQ ID NOs: 43 to 46, provided that the CDRs of said amino acid sequence exhibiting at least 80% identity are identical to those comprised in any one of SEQ ID NOs: 43 to 46, respectively. In SEQ ID NO: 43, the last three residues "GNS" are dispensable.

Preferred levels of sequence identity include at least 85%, at least 90%, at least 91%, at least 92%, at least 93%, at least 94%, at least 95%, at least 96%, at least 97%, at least 98%, and at least 99%. Means and methods for determining sequence identity are well-known in the art. A preferred algorithm for determining pairwise sequence identity is the basic local alignment search tool (BLAST) as described, for example, in McGinnis and Madden (Nucleic Acid Research 32, W20-W25 (2004)).

The location of said CDRs in a given sequence, in the present case in the sequences of SEQ ID NOs: 43 to 46 can be determined with art-established methods, known art-established methods including the systems of Chothia, Kabat and LeFranc/IMGT, respectively. In the absence of any indication to the contrary, it is understood that the CDRs according to the above defined particularly preferred embodiment are those defined above, namely a first set having the sequences of SEQ ID NOs: 1 to 6, 7 to 12 or 13 to 18, and a second set having the sequences of SEQ ID NOs: 19 to 24, 25 to 30, 31 to 36 or 37 to 42. As can be seen from the sequences as comprised in the enclosed sequence listing, these specific CDR sequences (underlined in the sequences reproduced further below) are indeed comprised in the sequences of SEQ ID NOs: 43 to 46.

The sequences of SEQ ID NOs: 1 to 6 define the CDRs and SEQ ID NOs: 37 to 40 define bispecific bivalent polypeptides capable of binding a specific epitope within the small surface antigen of HBV. This epitope is located in the a-determinant, which is exposed to the surface of infected cells and virions, respectively. The term "a-determinant" is used to designate a region within the small surface antigen of HBV where the main epitopes for induction of a protective humoral immune response are located. These CDRs as well as the polypeptides of SEQ ID NOs: 43 to 46 have the advantage they can be used for all HBV serotypes.

In a second aspect, the present invention provides a set of nucleic acids encoding the polypeptides constituting the binding molecule, which binding molecule is a multimer of polypeptides. Said second aspect, in an alternative, relates to a nucleic acid encoding the binding molecule, which is a—single—polypeptide. Preferred embodiments of the polypeptides give rise to corresponding preferred embodiments of said nucleic acid.

The term "nucleic acid" has its art-established meaning and is not particularly limited. Preferred are DNA such as genomic DNA or cDNA as well as RNA such as mRNA. While not being preferred, the use of nucleotide derivatives is envisaged which nucleotide derivatives include 2' derivatized nucleotides such as 2' methyl nucleotides; peptide nucleotides as the occur in peptide nucleic acids and the like.

In a further aspect, the present invention provides a pharmaceutical composition comprising or consisting of one or more binding molecules of the first aspect and/or one or more nucleic acids of the second aspect.

The pharmaceutical composition may further comprise pharmaceutically acceptable carriers, excipients and/or diluents. Examples of suitable pharmaceutical carriers, excipients and/or diluents are well known in the art and include phosphate buffered saline solutions, water, emulsions, such as oil/water emulsions, various types of wetting agents, sterile solutions etc. Compositions comprising such carriers can be formulated by well-known conventional methods. These pharmaceutical compositions can be administered to the subject at a suitable dose. Administration of the suitable compositions may be effected by different ways, e.g., by intravenous, subcutaneous or oral administration, these three options being preferred, and furthermore by intraperitoneal, intramuscular, topical, intradermal, intranasal or intrabronchial administration. Formulations for oral administration include tablets and syrups. It is particularly preferred that said administration is carried out by injection. The compositions may also be administered directly to the target site, e.g., by biolistic delivery to an external or internal target site. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Proteinaceous pharmaceutically active matter may be present in amounts between 1 ng and 10 mg/kg body weight per dose; however, doses below or above this exemplary range are envisioned, especially considering the aforementioned factors. If the regimen is a continuous infusion, it should also be in the range of 1 μg to 10 mg units per kilogram of body weight per minute.

Particularly preferred is intravenous administration.

In a further aspect, the present invention provides one or more binding molecules, nucleic acids and/or pharmaceutical compositions of the invention for use in a method of treating or preventing HBV infection and/or a condition caused by said HBV infection, said condition caused by said HBV infection being selected from liver cirrhosis, hepatocellular carcinoma, and liver cancer, said liver cancer being characterized by the expression of one or more HBV surface antigens. It is preferred that said hepatocellular carcinoma is characterized by the expression of one or more of the above defined HBV surface antigens.

In a further aspect, the present invention provides a method of treating or preventing HBV infection and/or a condition caused by said HBV infection, said condition caused by said HBV infection being selected from liver cirrhosis and hepatocellular carcinoma, said method comprising administering a therapeutically effective amount or a preventive amount, respectively, of one or more binding molecules, nucleic acids and/or pharmaceutical compositions of the invention to a patient in need thereof.

In an embodiment, said pharmaceutical composition, said binding molecule(s) and/or nucleic acid(s) for use in a method of treating and said method of treating, respectively, are such that the recited binding molecules and/or nucleic acids are the only pharmaceutically active agents comprised or used.

Having said that, it is also deliberately envisaged to incorporate one or more further pharmaceutically active agents in a combination therapy. Such further pharmaceutically active agents may be selected from interferons or other immunomodulators (such as e.g., interferon alpha 2a or 2b, interferon lambda), directly acting antivirals such as nucleos(t)ide analogues (such as e.g., Lamivudine (Epivir-HBV, Zeffix or Heptodin), Adefovir dipivoxil (Hepsera, Preveon), Entecavir (Baraclude, Entaliv), Telbivudine (Tyzeka, Sebivo), Tenofovir (Viread)), entry inhibitors (such as e.g., Myrcludex-B), other antivirals, or cytokines such as Interleukin-2.

Accordingly, it is envisaged that in said pharmaceutical composition and in accordance with said binding molecule(s) for use in a method of treating and said method of treating, the recited binding molecules, and furthermore one or more of the above defined specific pharmaceutically active agents are the only pharmaceutically active agents comprised or used.

Alternatively, yet further pharmaceutically active agents may be present. Additional ingredients or pharmaceutically active agents which enhance the stability of the binding molecule, such as proteins, e.g. milk proteins, nutrients or salt solutions might be added to increase bioavailability and/or half-life.

In a further aspect, the present invention provides an in vitro method of killing cells infected with HBV, said method comprising culturing said cells infected with HBV with (i) immune effector cells and (ii) one or more binding molecules of the invention.

In a preferred embodiment of the in vitro method, said immune effector cells (i) are comprised in peripheral blood mononuclear cells; or (ii) are or comprise NK cells and/or CTLs.

In a further aspect, the present invention provides an in vitro or ex vivo immune effector cell, which (a) has a binding molecule of the first aspect bound to a surface antigen of said immune effector cell; and/or (b) has been transformed, transfected or transduced with one or more nucleic acids according to the second aspect. Preferred immune effector cells and preferred surface antigens presented by immune effector cells are as defined above. Such immune effector cell is useful for administration to a patient suffering from HBV infection, liver cirrhosis or hepatocellular carcinoma. Accordingly provided is also a pharmaceutical composition comprising or consisting of an immune effector cell which has bound to a surface antigen thereof a binding molecule of the invention. Also provided is an immune effector cell which has bound to a surface antigen thereof a binding molecule of the invention for use in a method of treating or preventing HBV infection, liver cirrhosis or hepatocellular carcinoma.

The present invention extends to certain embodiments which are less preferred and accordingly may be excluded from broader embodiments by means of a proviso.

Less preferred in accordance with the present invention is a trispecific and tetravalent binding molecule consisting of a first and a second polypeptide, said first and second polypeptides each being bispecific and bivalent, wherein the first specificity of either polypeptide is for a HBV surface antigen selected from HBV small surface antigen; HBV medium surface antigen; and HBV large surface antigen and the second specificity is for CD3 and CD28, respectively.

Even less preferred in this regard is a trispecific and tetravalent binding molecule consisting of a first and a second polypeptide, said first and second polypeptides each being bispecific and bivalent, wherein said first and said second polypeptide are bound to each other non-covalently, and wherein the first specificity of either polypeptide is for a HBV surface antigen selected from HBV small surface antigen; HBV medium surface antigen; and HBV large surface antigen and the second specificity is for CD3 and CD28, respectively.

Particularly less preferred is a trispecific and tetravalent binding molecule consisting of a first and a second polypeptide, said first and second polypeptides each being bispecific and bivalent, wherein there is at least one covalent linkage between said first and said second polypeptide, preferably at least one disulfide bridge between a Cys residue of said first polypeptide and a Cys residue of said second polypeptide, and wherein the first specificity of either polypeptide is for a HBV surface antigen selected from HBV small surface antigen; HBV medium surface antigen; and HBV large antigen and the second specificity is for CD3 and CD28, respectively.

Especially less preferred is a trispecific and tetravalent binding molecule consisting of a first and a second polypeptide, said first and second polypeptides each being bispecific and bivalent, wherein there are two disulfide bonds between said first and said second polypeptide, and wherein the first specificity of either polypeptide is for a HBV surface antigen selected from HBV small surface antigen; HBV medium surface antigen; and HBV large surface antigen and the second specificity is for CD3 and CD28, respectively.

In relation to each of the above defined less preferred embodiments, it is particularly less preferred that the binding sites on first and second polypeptide are provided by scFv fragments. Furthermore, it is particularly less preferred in relation with any of the preceding less preferred embodiments that in both of said first and second polypeptide there is a CH2 and CH3 domain between the two scFv fragments providing the binding sites.

Accordingly, especially less preferred is a trispecific and tetravalent binding molecule consisting of a first and a second polypeptide, said first and second polypeptides each being bispecific and bivalent, wherein there are two disulfide bonds between said first and said second polypeptide, wherein the first specificity of either polypeptide is for a HBV surface antigen selected from HBV small surface antigen; HBV medium surface antigen; and HBV large surface antigen and the second specificity is for CD3 and CD28, respectively, wherein the binding sites on first and second polypeptide are provided by scFv fragments, and wherein in both of said first and second polypeptide there is a CH2 and CH3 domain between the two scFv fragments providing the binding sites.

Thus, to give an example, the present invention also provides a binding molecule comprising at least three binding specificities, wherein (a) the first specificity is for a Hepatitis B virus (HBV) surface antigen selected from HBV small surface antigen, HBV medium surface antigen and HBV large surface antigen; (b) (i) the second and third specificity are for CD3 and CD28, respectively; or (ii) the second and third specificity are selected from specificities for CD16, CD56, NKp30, NKp46, 4-1BB and NKG2D; and (c) each binding specificity is provided by one or more binding sites, each binding site being independently provided by (i) a set of six complementarity determining regions (CDRs), wherein said set of six CDRs consists of a first set of three CDRs and a second set of three CDRs, wherein said first and said second set is each comprised in an immunoglobulin domain; or (ii) a set of three CDRs, wherein said set of three CDRs is comprised in an immunoglobulin domain; provided that trispecific and tetravalent binding molecules consisting of a first and a second polypeptide, said first and second polypeptides each being bispecific and bivalent, wherein there are two disulfide bonds between said first and said second polypeptide, wherein the first specificity of either polypeptide is for a HBV surface antigen selected from HBV small surface antigen; HBV medium surface antigen; and HBV large surface antigen and the second specificity is for CD3 and CD28, respectively, wherein the binding sites on first and second polypeptide are provided by scFv fragments, and wherein in both of said first and second polypeptide there is a CH2 and CH3 domain between the two scFv fragments providing the binding sites, are excluded.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

Sequences disclosed in this application:

```
C8 HC CDR1
                                              SEQ ID NO 1
Gly Phe Thr Phe Ser Gly Tyr Ala

C8 HC CDR2
                                              SEQ ID NO 2
Ile Ser Gly Ser Gly Gly Ser Thr

C8 HC CDR3
                                              SEQ ID NO 3
Ala Lys Pro Pro Gly Arg Gln Glu Tyr Tyr Gly Ser

Ser Ile Tyr Tyr Phe Pro Leu Gly Asn

C8 LC CDR1
                                              SEQ ID NO 4
Asn Ile Gly Ser Lys Ser

C8 LC CDR2
                                              SEQ ID NO 5
Asp Asp Ser

C8 LC CDR3
                                              SEQ ID NO 6
Gln Val Trp Asp Ser Ser Ser Asp Leu Val Val
```

```
5F9 HC CDR1
                                        SEQ ID NO 7
Gly Phe Thr Phe Asn Asn Tyr Ala

5F9 HC CDR2
                                        SEQ ID NO 8
Ile Asn Ser Asp Gly Arg Ser Thr

5F9 HC CDR3
                                        SEQ ID NO 9
Ala Arg Thr Phe Tyr Ala Asp Tyr

5F9 LC CDR1
                                        SEQ ID NO 10
Gln Asn Val Asp Thr Thr

5F9 LC CDR2
                                        SEQ ID NO 11
Trp Ala Ser

5F9 LC CDR3
                                        SEQ ID NO 12
Gln Gln Tyr Ser Ile Phe Pro Tyr Thr

5A19 HC CDR1
                                        SEQ ID NO 13
Gly Phe Thr Phe Ser Ser Tyr Ala

5A19 HC CDR2
                                        SEQ ID NO 14
Val Ser Ser Asp Gly Ser Tyr Ala

5A19 HC CDR3
                                        SEQ ID NO 15
Ala Ser Phe Asn Trp Asp Val Ala Tyr

5A19 LC CDR1
                                        SEQ ID NO 16
Gln Ser Leu Leu Asn Thr Arg Thr Arg Lys Ser Tyr

5A19 LC CDR2
                                        SEQ ID NO 17
Trp Ala Ser

5A19 LC CDR3
                                        SEQ ID NO 18
Lys Gln Ser Tyr Ser Leu Tyr Thr

OKT3 HC CDR1
                                        SEQ ID NO 19
Gly Tyr Thr Phe Thr Arg Tyr Thr

OKT3 HC CDR2
                                        SEQ ID NO 20
Ile Asn Pro Ser Arg Gly Tyr Thr

OKT3 HC CDR3
                                        SEQ ID NO 21
Ala Arg Tyr Tyr Asp Asp His Tyr Cys Leu Asp Tyr

OKT3 LC CDR1
                                        SEQ ID NO 22
Ser Ser Val Ser Tyr

OKT3 LC CDR2
                                        SEQ ID NO 23
Asp Thr Ser

OKT3 LC CDR3
                                        SEQ ID NO 24
Gln Gln Trp Ser Ser Asn Pro Phe Thr 9.3 HC CDR1
                                        SEQ ID NO 25
Gly Phe Ser Leu Ser Asp Tyr Gly 9.3 HC CDR2
                                        SEQ ID NO 26
Ile Trp Ala Gly Gly Gly Thr 9.3 HC CDR3
                                        SEQ ID NO 27
Ala Arg Asp Lys Gly Tyr Ser Tyr Tyr Tyr Ser Met
Asp Tyr 9.3 LC CDR1
                                        SEQ ID NO 28
Glu Ser Val Glu Tyr Tyr Val Thr Ser Leu 9.3 LC CDR2
                                        SEQ ID NO 29
Ala Ala Ser 9.3 LC CDR3
                                        SEQ ID NO 30
Gln Gln Ser Arg Lys Val Pro Tyr Thr

A9 HC CDR
                                        SEQ ID NO 31
Gly Tyr Thr Phe Thr Asn Tyr Trp

A9 HC CDR2
                                        SEQ ID NO 32
Ile Tyr Pro Gly Gly Gly Tyr Thr

A9 HC CDR3
                                        SEQ ID NO 33
Ala Arg Ser Ala Ser Trp Tyr Phe Asp Val

A9 LC CDR1
                                        SEQ ID NO 34
Thr Gly Thr Val Thr Thr Ser Asn Tyr

A9 LC CDR2
                                        SEQ ID NO 35
His Thr Asn

A9 LC CDR3
                                        SEQ ID NO 36
Ala Leu Trp Tyr Asn Asn His Trp Val

NCAM29.2 HC CDR1
                                        SEQ ID NO 37
Gly Phe Thr Phe Ser Ser Phe Gly

NCAM29.2 HC CDR2
                                        SEQ ID NO 38
Ile Ser Ser Gly Ser Tyr Ala Ile

NCAM29.2 HC CDR3
                                        SEQ ID NO 39
Val Arg Gly Arg Arg Leu Gly Glu Gly Tyr Ala Met
Asp Tyr

NCAM29.2 LC CDR1
                                        SEQ ID NO 40
Gln Ser Leu Leu Tyr Ser Ser Asn Gln Lys Asn Tyr

NCAM29.2 LC CDR2
                                        SEQ ID NO 41
Trp Ala Ser

NCAM29.2 LC CDR3
                                        SEQ ID NO 42
Gln Gln Tyr Ser Ser Trp Thr

C8-hIgG1Fc$_{mut}$-OKT3
                                        SEQ ID NO 43
MDFEVQIFSFLLISASVIMSRMAEVQLVESGGGLLQPGGSLRLSCAASGF
TFSGYAMSWVRQAPGKGLEWVSSISGSGGSTYYADSVKGRFTISRDNSKN
TLYLQMNSLRAEDTALYYCAKPPGRQEYYGSSIYYFPLGNWGQGTLVTVS
SASTKGPKLEEGEFSEARVQSALTQPASVSAPGQTARITCGGNNIGSKS
VHWYQQKPGQAPVLVVYDDSDRPSGIPERFSGSNSGNTATLTISRVEAGD
EADYYCQVWDSSSDLVVFGGGTKLTVLGNSGGGGSGGGGSGGGGSASEPK
```

-continued
SSDKTHT<u>C</u>PP<u>C</u>PAPPAAGPSVFLFPPKPKDTLMISRTPEVTCVVVDVSH
EDPEVKFNWYVDGVEVHNAKTKPREEQYNSTYRVVSVLTVLHQDWLNGKE
YKCAVSNKGLASSIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK*DPGWSHPQFEKSRGGGG*QVQ
LQQSGAELARPGASVKMSCKAS<u>GYTFTRYT</u>MHWVKQRPGQGLEWIGY<u>INP</u>
<u>SRGYT</u>NYNQKFKDKATLTTDKSSSTAYMQLSSLTSEDSAVYYC<u>ARYYDDH</u>
<u>YCLDY</u>WGQGTTLTVSS*GNSGGGGSGGGGSGGGGSAS*QIVLTQSPAIMSAS
PGEKVTMTCSAS<u>SSVSY</u>MNWYQQKSGTSPKRWIY<u>DTS</u>KLASGVPAHFRGS
GSGTSYSLTISGMEAEDAATYYC<u>QQWSSNPFT</u>FGSGTKLEINGNS
C8-hIgG1Fc*<sub>mut</sub>*-9.3

SEQ ID NO 44
MDFEVQIFSFLLISASVIMSRMAEVQLVESGGGLLQPGGSLRLSCAAS<u>GF</u>
<u>TFSGYA</u>MSWVRQAPGKGLEWVSS<u>ISGSGGST</u>YYADSVKGRFTISRDNSKN
TLYLQMNSLRAEDTALYYC<u>AKPPGRQEYYGSSIYYFPLGN</u>WGQGTLVTVS
S*ASTKGPKLEEGEFSEAR*VQSALTQPASVSVAPGQTARITCGGN<u>NIGSKS</u>
VHWYQQKPGQAPVLVVY<u>DDS</u>DRPSGIPERFSGSNSGNTATLTISRVEAGD
EADYYC<u>QVWDSSSDLVV</u>FGGGTKLTVLGN*SGGGGSGGGGSGGGGSAS*EPK
SSDKTHT<u>C</u>PP<u>C</u>PAPPAAGPSVFLFPPKPKDTLMISRTPEVTCVVVDVSH
EDPEVKFNWYVDGVEVHNAKTKPREEQYNSTYRVVSVLTVLHQDWLNGKE
YKCAVSNKGLASSIEKTISKAKGQPREPQVYTLPPSRDELTKNQVSLT
CLVKGFYPSDIAVEWESNGQPENNYKTTPPVLDSDGSFFLYSKLTVDKSR
WQQGNVFSCSVMHEALHNHYTQKSLSLSPGK*DPGWSHPQFEKSSGGGG*QV
QLQESGPGLVTPSQSLSITCTVS<u>GFSLSDYG</u>VHWVRQSPGQGLEWLGV<u>IW</u>
<u>AGGGTNYNSALMSR</u>KSISKDNSKSQVFLKMNSLQADDTAVYYC<u>ARDKGYS</u>
<u>YYYSMDY</u>WGQGTTVTVSS*RGGGSGGGGSGGGGS*DIELTQSPASLAVSLGQ
RATISCRAS<u>ESVEYYVTSL</u>MQWYQQKPGQPPKLLIF<u>AAS</u>NVESGVPARFS
GSGSGTNFSLNIHPVDEDDVAMYFC<u>QQSRKVPYT</u>FGGGTKLEIKR
C8-hIgG1Fc*<sub>mut</sub>*-A9

SEQ ID NO 45
MDFEVQIFSFLLISASVIMSRMAEVQLVESGGGLLQPGGSLRLSCAAS<u>GF</u>
<u>TFSGYA</u>MSWVRQAPGKGLEWVSS<u>ISGSGGST</u>YYADSVKGRFTISRDNSKN
TLYLQMNSLRAEDTALYYC<u>AKPPGRQEYYGSSIYYFPLGN</u>WGQGTLVTVS
S*ASTKGPKLEEGEFSEAR*VQSALTQPASVSVAPGQTARITCGGN<u>NIGSKS</u>
VHWYQQKPGQAPVLVVY<u>DDS</u>DRPSGIPERFSGSNSGNTATLTISRVEAGD
EADYYC<u>QVWDSSSDLVV</u>FGGGTKLTVL*GNSGGGGSGGGGSGGGGSAS*EPK
SSDKTHT<u>C</u>PP<u>C</u>PAPPAAGPSVFLFPPKPKDTLMISRTPEVTCVVVDVSH
EDPEVKFNWYVDGVEVHNAKTKPREEQYNSTYRVVSVLTVLHQDWLNGKE
YKCAVSNKGLASSIEKTISKAKGQPREPQVYTLPPSRDELTKNQVSLT
CLVKGFYPSDIAVEWESNGQPENNYKTTPPVLDSDGSFFLYSKLTVDKSR
WQQGNVFSCSVMHEALHNHYTQKSLSLSPGK*DPGWSHPQFEKSRGGGG*QV
QLQQSGAELVRPGTSVKISCKAS<u>GYTFTNYW</u>LGWVKQRPGHGLEWIGD<u>IY</u>

<u>PGGGYT</u>NYNEKFKGKATVTADTSSRTAYVQVRSLTSEDSAVYFC<u>ARSASW</u>
<u>YFDV</u>WGAGTTVTVSS*GNSGGGGSGGGGSGGGGSASQ*AVVTQESALTTSPG
ETVTLTCRSN<u>TGTVTTSNY</u>ANWVQEKPDHLFTGLIGHTNNRAPGVPARFS
GSLIGDKAALTITGAQTEDEAIYFC<u>ALWYNNHWV</u>FGGGTKLTVL
C8-hIgG1Fc*<sub>mut</sub>*-NCAM29.2

SEQ ID NO 46
MDFEVQIFSFLLISASVIMSRMAEVQLVESGGGLLQPGGSLRLSCAAS<u>GF</u>
<u>TFSGYA</u>MSWVRQAPGKGLEWVSS<u>ISGSGGST</u>YYADSVKGRFTISRDNSKN
TLYLQMNSLRAEDTALYYC<u>AKPPGRQEYYGSSIYYFPLGN</u>WGQGTLVTVS
S*ASTKGPKLEEGEFSEAR*VQSALTQPASVSVAPGQTARITCGGN<u>NIGSKS</u>
VHWYQQKPGQAPVLVVY<u>DDS</u>DRPSGIPERFSGSNSGNTATLTISRVEAGD
EADYYC<u>QVWDSSSDLVV</u>FGGGTKLTVL*GNSGGGGSGGGGSGGGGSAS*EPK
SSDKTHT<u>C</u>PP<u>C</u>PAPPAAGPSVFLFPPKPKDTLMISRTPEVTCVVVDVSH
EDPEVKFNWYVDGVEVHNAKTKPREEQYNSTYRVVSVLTVLHQDWLNGKE
YKCAVSNKGLASSIEKTISKAKGQPREPQVYTLPPSRDELTKNQVSLT
CLVKGFYPSDIAVEWESNGQPENNYKTTPPVLDSDGSFFLYSKLTVDKSR
WQQGNVFSCSVMHEALHNHYTQKSLSLSPGK*DPGWSHPQFEKSSGGG*DVQ
LVESGGGLVQPGGSRKLSCAAS<u>GFTFSSFG</u>MHWVRQAPEKGLEWVAY<u>ISS</u>
<u>GSYAI</u>YYADTVKGRFTISRDNPENTLFLQMTSLRSEDSAMYYC<u>VRGRRLG</u>
<u>EGYAMDY</u>WGQGTSVTVSS*GNSGGGGSGGGGSGGGGSAS*DIVMSQSPSSLA
VSVGEKVTMSCKSS<u>QSLLYSSNQKNY</u>LAWYQQKPGQSPKLLIY<u>WAS</u>TRKS
GVPDRFTGSGSGTDFTLTISSVKAEDLAVYYC<u>QQYSSWT</u>FGGGTKLEIKR

SEQ ID NO 47
Gly Gly Gly Gly Ser Gly Gly Gly Gly Ser Gly Gly
Gly Gly Ser

SEQ ID NO 48
Ala Lys Thr Thr Pro Lys Leu Glu Glu Gly Glu Phe
Ser Glu Ala Arg Val

SEQ ID NO 49
Gly Gly Gly Gly Ser Gly Gly Gly Gly Ser Gly Gly
Gly Gly Ser Gly Gly Gly Gly Ser

SEQ ID NO 50
C8-hIgG1Fc*<sub>mut</sub>*-OKT3 with Jun leucine zipper
dimerization domain (bold face italics underlined)
MDFEVQIFSFLLISASVIMSRMAEVQLVESGGGLLQPGGSLRLSCAAS<u>G</u>
<u>FTFSGYA</u>MSWVRQAPGKGLEWVSS<u>ISGSGGST</u>YYADSVKGRFTISRDNS
KNTLYLQMNSLRAEDTALYYC<u>AKPPGRQEYYGSSIYYFPLGN</u>WGQGTLV
TVSS*ASTKGPKLEEGEFSEAR*VQSALTQPASVSVAPGQTARITCGGN<u>NI</u>
<u>GSKS</u>VHWYQQKPGQAPVLVVY<u>DDS</u>DRPSGIPERFSGSNSGNTATLTISR
VEAGDEADYYC<u>QVWDSSSDLVV</u>FGGGTKLTVL*GNSGGGGSGGGGSGGGG*
*SAS**<u>RIARLEEKVKTLKAQNSELASTANMLREQVAQIKQKVMNY</u>*SSEPKS
SDKTHT<u>C</u>PP<u>C</u>PAPPAAGPSVFLFPPKPKDTLMISRTPEVTCVVVDVSHE
DPEVKFNWYVDGVEVHNAKTKPREEQYNSTYRVVSVLTVLHQDWLNGKE
YKCAVSNKGLASSIEKTISKAKGQPREPQVYTLPPSRDELTKNQVSLTC

```
-continued
LVKGFYPSDIAVEWESNGQPENNYKTTPPVLDSDGSFFLYSKLTVDKSR

WQQGNVFSCSVMHEALHNHYTQKSLSLSPGK*DPGWSHPQFEKSRGGGGQ*

VQLQQSGAELARPGASVKMSCKAS<u>GYTFTRYT</u>MHWVKQRPGQGLEWIGY

<u>INPSRGYTNYNQKFKD</u>KATLTTDKSSSTAYMQLSSLTSEDSAVYYC<u>ARY

YDDHYCLDY</u>WGQGTTLTVS*SGNSGGGGSGGGGSGGGGS*ASQIVLTQSPA

IMSASPGEKVTMTCSAS<u>SSVSY</u>MNWYQQKSGTSPKRWIY<u>DTS</u>KLASGVP

AHFRGSGSGTSYSLTISGMEAEDAATYYC<u>QQWSSNPFT</u>FGSGTKLEING

NS
```

```
                                            SEQ ID NO 51
C8-hIgG1Fc_mut-9.3 with Fos leucine zipper
dimerization domain (bold face italics underlined)
MDFEVQIFSFLLISASVIMSRMAEVQLVESGGGLLQPGGSLRLSCAAS<u>G FTFSGYA</u>MSWVRQAPGKGLEWVSS<u>ISGSGGST</u>YYADSVKGRFTISRDNS KNTLYLQMNSLRAEDTALYYC<u>AKPPGRQEYYGSSIYYFPLGN</u>WGQGTLV TVSS*ASTKGPKLEEGEFSEARV*QSALTQPASVSVAPGQTARITCGGN<u>NI GSKS</u>VHWYQQKPGQAPVLVVY<u>DDS</u>DRPSGIPERFSGSNSGNTATLTISR VEAGDEADYYC<u>QVWDSSSDLVV</u>FGGGTKLTVL*GNSGGGGSGGGGSGGGG SAS*<u>*LTDTLQAETDQLEDKKSALQTEIANLLKEKEKLEFILAAY*</u>SSEPKS

*S*DKTHT<u>C</u>PP<u>C</u>PAPP*AA*GPSVFLFPPKPKDTLMISRTPEVTCVVVDVSHE

DPEVKFNWYVDGVEVHNAKTKPREEQYNSTYRVVSVLTVLHQDWLNGKE

YKC<u>A</u>VSNK*GL***AS*S*IEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPGKDPGWSHPQFEKSSGGGGQ

VQLQESGPGLVTPSQSLSITCTVS<u>GFSLSDYG</u>VHWVRQSPGQGLEWLGV

<u>IWAGGGT</u>NYNSALMSRKSISKDNSKSQVFLKMNSLQADDTAVYYC<u>ARDK

GYSYYYSMDY</u>WGQGTTVTVSSRGGGSGGGGSGGGGSDIELTQSPASLAV

SLGQRATISCRAS<u>ESVEYYVTSL</u>MQWYQQKPGQPPKLLIF<u>AAS</u>NVESGV

PARFSGSGSGTNFSLNIHPVDEDDVAMYFC<u>QQSRKVPYT</u>FGGGTKLEIK

R
```

(B) Granzyme B expression indicating cytotoxic activation. TriMAB and OKTA trispecific antibody constructs induced a significantly higher levels of cytotoxic activation, with TriMAb being the most potent construct inducing granzyme B expression in 95% of CD8+ T cells.

Figure 5:
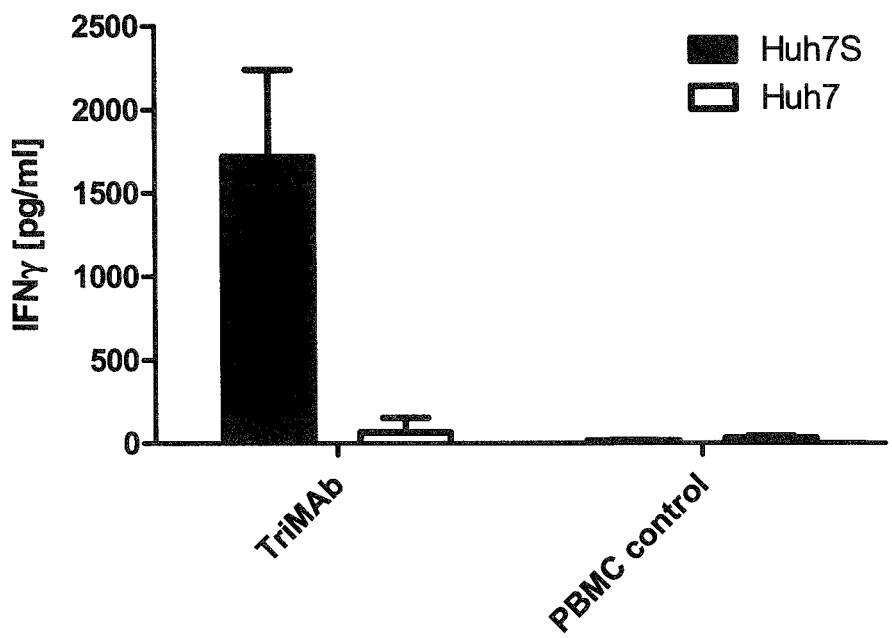

FIG. 5: Naïve T cells from healthy donors are activated by the TriMAb. IFNγ-secretion in PBMC from healthy donors when co-cultured with HBsAg-positive (Huh7S) or – negative (Huh7) target cells in the presence of TriMAb. Only when the TriMAb was added and target cells express HBsAg an activation of T cells as determined by secretion of IFNγ was detected.

Figure 6:
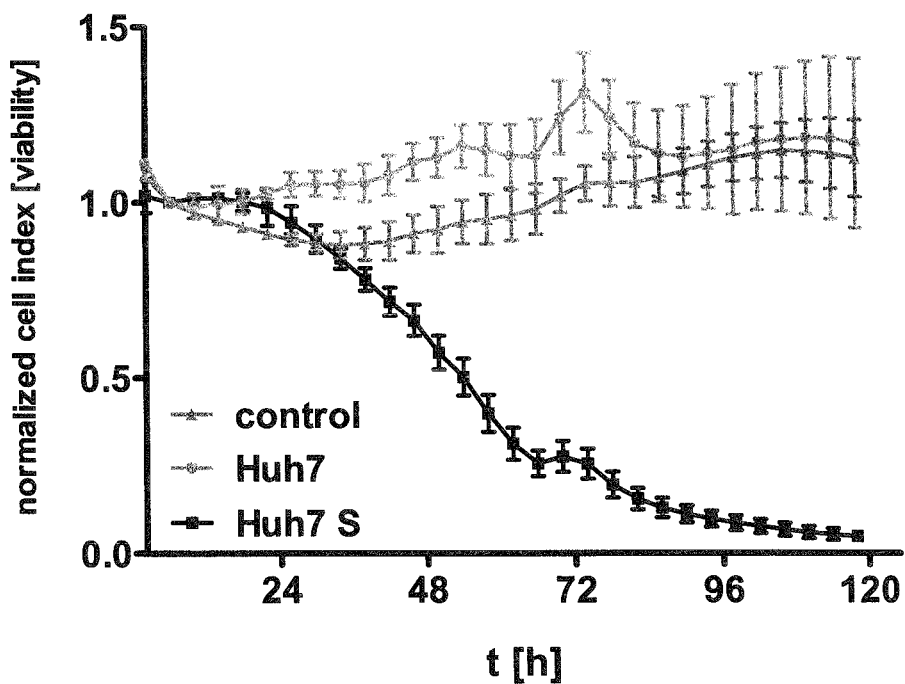

FIG. 6: Naïve T cells from healthy donors are activated to kill HBsAg-positive target cells by the TriMAb. Co-culture of PBMC from healthy donors with HBSAg-negative (Huh7) and HBsAg-positive target cells (Huh7S). After addition of TriMAb cell viability was determined by the XCelligence assay over time in triplicate. In PBMC control, cells were co-cultured with Huh7S cells but no antibody was added. Only when the TriMAb was added and target cells expressed HBsAg a specific killing was observed starting 24 hours after addition of the antibody.

Figure 7:
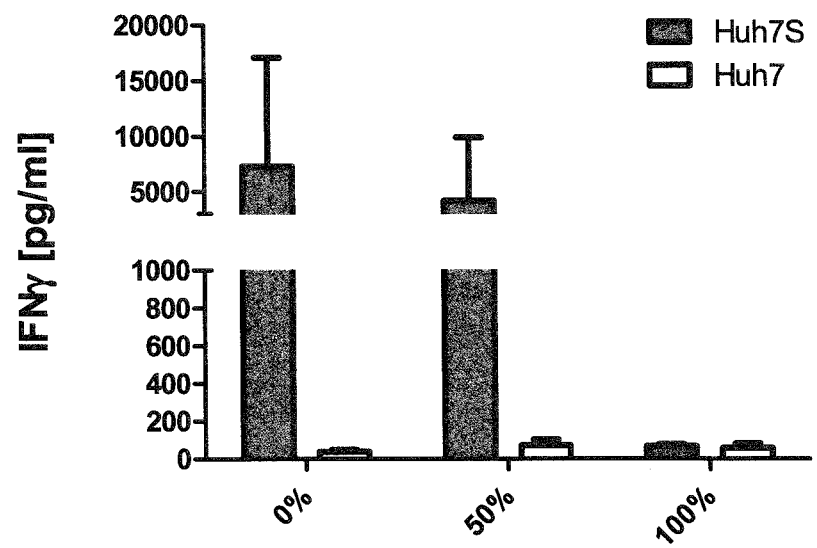
Figure 7:
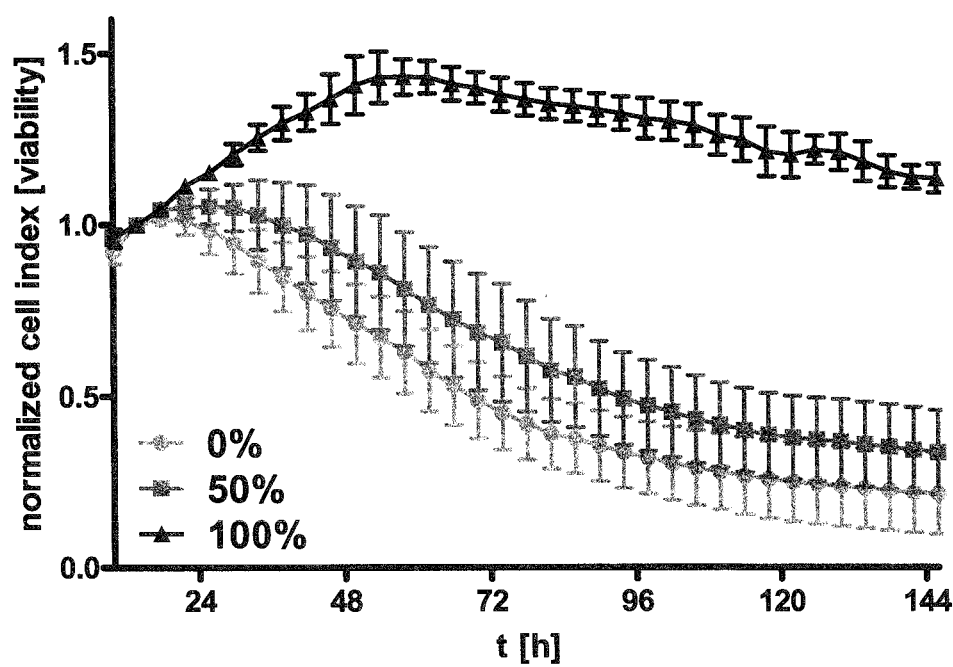

FIG. 7: Neutralizing anti-HBs antibodies compete with activation of T cells by TriMAb. Co-culture of TriMAb-treated PMBCs with HBsAg-positive Huh7 (Huh7S) cells in the presence of human serum containing neutralizing αHBs antibodies. 0%: Co-culture without Ab-containing serum; 50%: Half of the FCS was replaced by Ab-containing human serum resulting in an αHBs concentration of 117.5 IU/L; 100%: FCS was replaced by Ab-containing serum resulting in an αHBs concentration of 235 IU/L. (A) Without the addition of neutralizing antibodies, T cells were activated and secreted IFNγ and other cytokines and (B) T cells were activated to kill the target cells in a time typical course resulting in 50% loss of cell viability within 72 h. Neutralizing antibodies competed with TriMAb activity, resulting in a partial or even complete loss of T cell activation and cytotoxicity.

Figure 8:
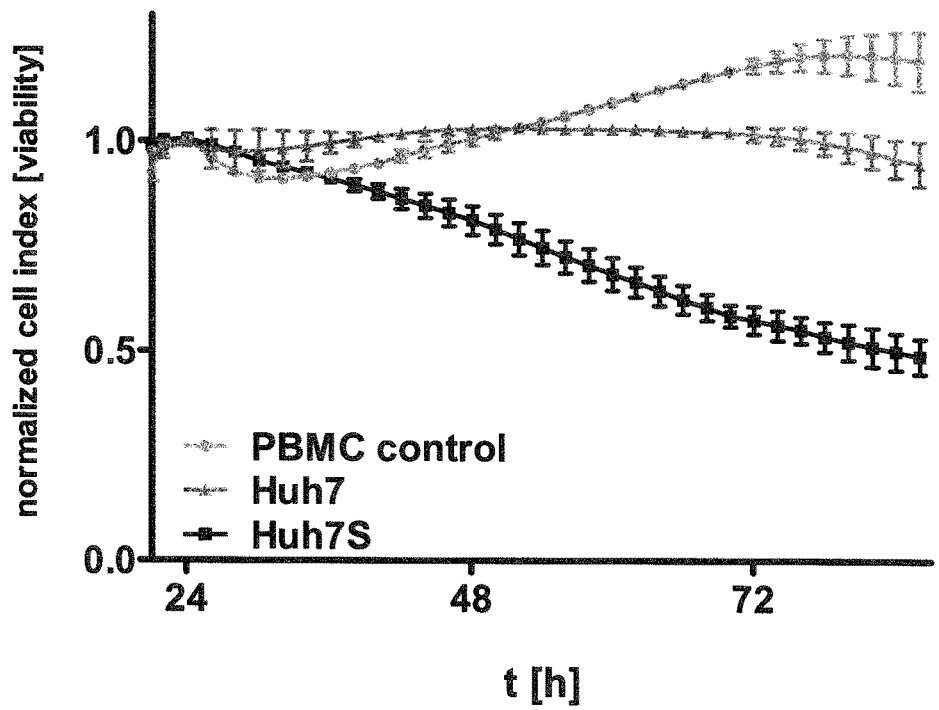

FIG. 8: PBMC from patients with chronic hepatitis B kill HBsAg-positive target cells when activated by the TriMAb. Co-culture of PBMC from patients with chronic hepatitis B (CHB) with HBSAg-negative (Huh7) and HBsAg-positive target cells (Huh7S). After addition of TriMAb cell viability was determined by the XCelligence assay over time in triplicate. In PBMC control, cells were co-cultured with Huh7S cells but no antibody was added. Only when the TriMAb was added and target cells expressed HBsAg a specific killing was observed starting 24-30 hours after addition of the antibody.

Figure 9:
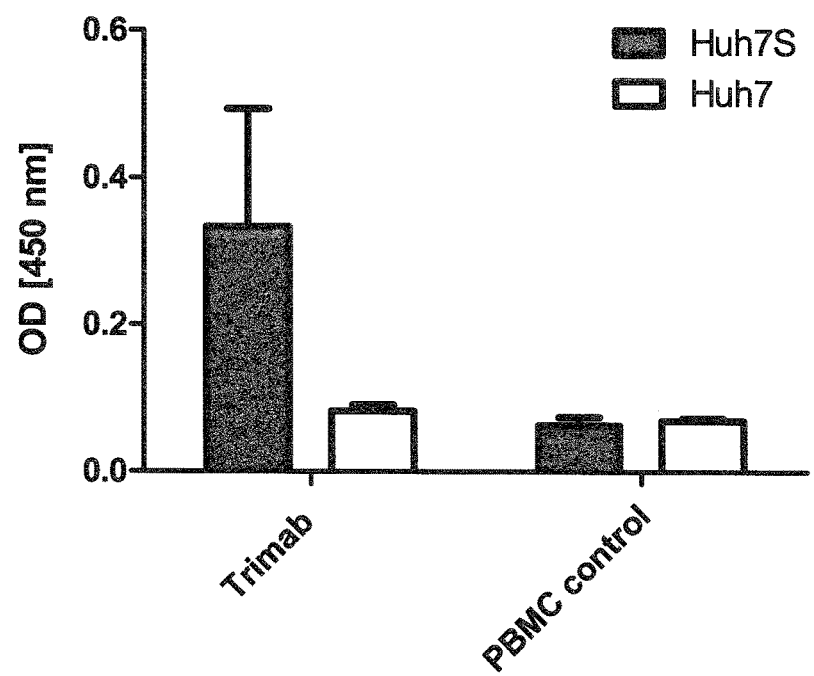

FIG. 9: PBMC from patients with chronic hepatitis B are activated by the TriMAb. IFNγ-secretion of PBMCs from patients with chronic hepatitis B (CHB), co-cultured with HBsAg-positive (Huh7S) or —negative (Huh7) target cells in the presence of TriMAb. Only when the TriMAb was added and target cells express HBsAg, an activation of T cells as determined by secretion of IFNγ was detected.

Figure 10A:
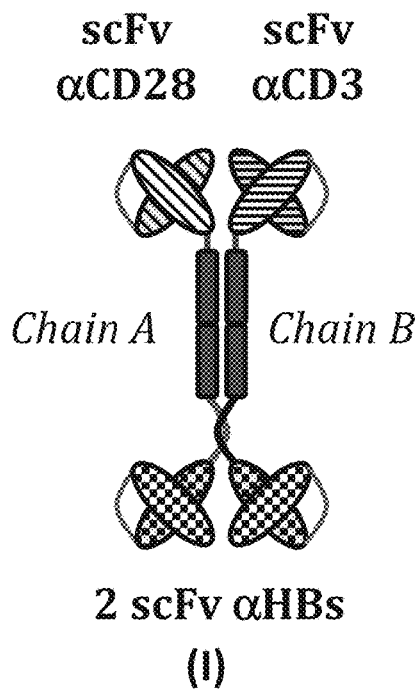
Figure 10B:
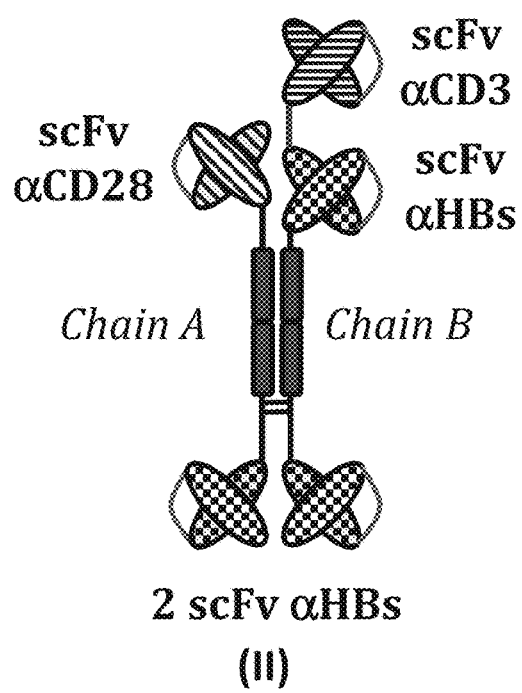
Figure 10C:
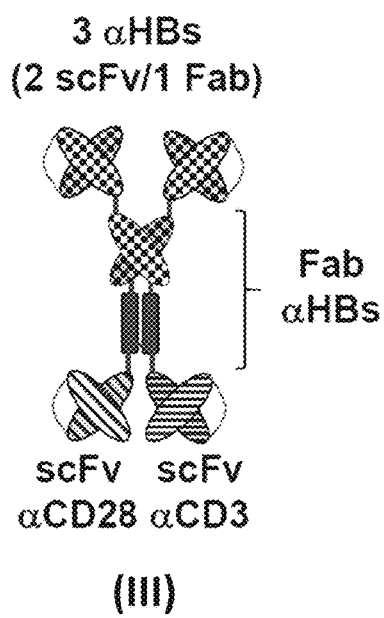
Figure 10C:
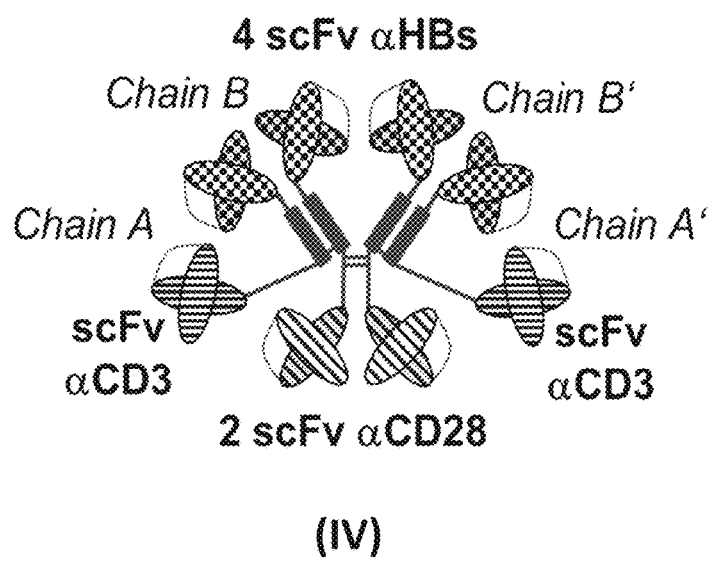
Figure 10E:
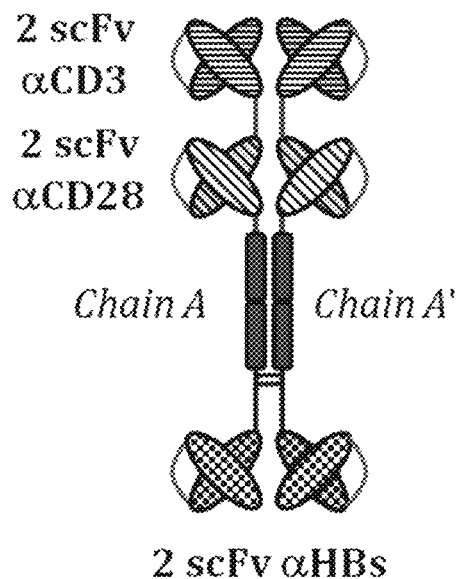
Figure 10F:
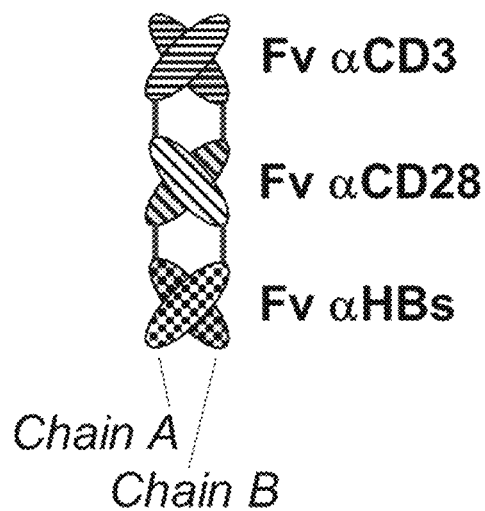
Figure 10G:
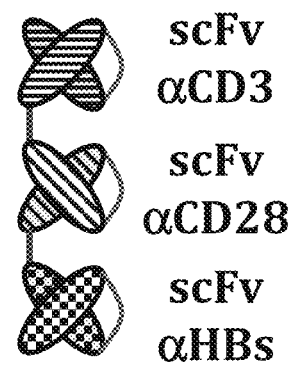

FIGS. 10A-10G shows exemplary binding molecules of the invention. FIG. 10A shows an exemplary binding molecule of structure (I). FIG. 10B shows an exemplary binding molecule of structure (II). FIG. 10C shows an exemplary binding molecule of structure (III). FIG. 10D shows an exemplary binding molecule of structure (IV). FIG. 10E shows an exemplary binding molecule of structure (V). FIG. 10F shows an exemplary binding molecule of structure (VI). FIG. 10G shows an exemplary binding molecule of structure (VII).

DETAILED DESCRIPTION OF EXEMPLARY EMBODIMENTS OF THE INVENTION

Example 1

Materials and Methods

Cloning and Production of Trispecific Antibodies

Complementary DNAs coding for variable heavy and variable light chains of anti-CD3 (OKT3), ad anti-CD28 (9.3) were obtained by PCR amplification of reverse-transcribed mRNAs from the respective hybridoma using a set of primers covering all VH and V |N | subtypes. PCR products were ligated into pCR2.1-TOPO (Invitrogen, Life Technologies) and sequenced. The anti-HBsAg scFv C8 was selected from a cDNA library of B cells from a hepatitis B vaccinee using phage display technology and codon-optimized. Using primers containing appropriate restriction sites in the 5' and 3' flanks variable heavy and variable light chain cDNAs coding for the above mentioned antibodies were assembled with a glycine-serine linker into scFvs. To obtain a pentavalent molecule, OKT3 and 9.3 scFvs were fused to the C-termini of the Fab fragment of antibody 5F9 while two entities of scFv C8 were added to its N-termini. To obtain an octavalent molecule four scFv C8 domains and two domains of OKT3 and 9.3, respectively, were liked to an IgG like molecule.

The C8 scFv coding sequence was cloned at the 5' end of the mentioned 5' glycine-serine linker. The complete scFv-linker-hIgG1Fc-linker-scFv sequence was subcloned into the mammalian expression vector pcDNA3.1(−) (Invitrogen). Maxi-prep plasmid DNA was used for transfection of HEK293 cells using the peqFECT transfection reagent (Peqlab). Stable transfectants were selected using 0.8-1.0 mg/ml G418 and expanded. Supernatants from HEK transfectants were collected and analyzed by ELISA for the concentration of secreted, trispecific antibodies and by Western blot for the integrity of the secreted antibodies using goat anti-human IgG-Fc specific, peroxidase-labeled antibodies.

Cell Culture Conditions and Generation of Huh7S cells

HuH7 hepatoma cells (Nakabayaski, et al. 1982. Growth of human hepatoma cell lines with differentiated functions in chemically defined medium. Cancer Res. 42: 3858-3863) and HEK293 cells were maintained in Dulbecco's modified Eagle medium (DMEM) supplemented with 10% fetal bovine serum (FBS), penicillin (100 U/mL), streptomycin (100 μg/mL), and L-glutamine (2 mmol/L) (all from GIBCO, Life Technologies).

To generate Huh7S cells, Huh-7 cells were transfected with a plasmid encoding the small HBV surface antigen of HBV genotype D subtype ayw1 and an antibiotic resistance gene using FuGene transfection reagent (Promega). After antibiotic selection, single cell clones were isolated and grown in 24 well plates. The clones with highest HBsAg secretion were selected and used to establish cell line Huh7-S used as target cells.

Isolation of PBMC

Peripheral blood mononuclear cells (PBMC) were isolated through density gradient centrifugation from heparinized whole blood using LSM 1077 Lymphocyte Separation Medium (PAA). 25 ml of blood was layered above 13 ml of LSM 1077. After centrifugation at 2000 rpm for 20 min (without break) at room temperature PBMC were harvested and cultured in RPMI 1640 medium supplemented with 10% fetal bovine serum (FBS), penicillin (100 U/mL), streptomycin (100 μg/ml), and L-glutamine (2 mmol/l) (all from GIBCO). After an overnight resting step at 37° C. in 5% CO2 PBMC were used for co-culture experiments.

Culture of PBMCs on Immobilized HBsAg

100 μl of recombinant HBsAg in PBS (5 μg/ml) was transferred to a 96-well plate and coated at 4° C. over night. The next day HBsAg-solution was decanted and the plate was washed with phosphate buffered saline. 1×105 PBMCs/well were transferred onto the HBsAg-coated plate and mixed with 100 μl of trispecific antibody containing supernatant. Wells without immobilized HBsAg served as a negative control. PBMC were cultured on plate-bound HBsAg for 48 h before the supernatant and cells were harvested for further analysis. Cytokine secretion resulting from activation of effector T cells was detected in the supernatant by ELISA using the Human IFN-γ ELISA MAX™ (BioLegend). Cells were stained with antibodies against LAMP-1 and granzyme B and analyzed by flow cytometry. All experiments were done in triplicates.

Co-Culture of HBV-Positive Target Cells and Redirected Effector Cells

Huh7 or Huh7S target cells were cultured in a 96 well plate at confluency. 1×105 PBMC cells were added in a volume of 100 μl medium per well. 100 μl of the HEK supernatants containing the trispecific antibodies were applied per well. For determination of synergistic effects of CD3 and CD28 activation, 50 μl of each bispecific antibody supernatant was added per well. Untreated target cells incubated with effector cells alone (without the addition of antibodies) served as negative control. After 96 or 120 hours, supernatant was collected and IFNγ secretion was analyzed by ELISA (see above).

To determine cytotoxicity, HBsAg-expressing Huh7S cells were cultured in the 96-well E-plate, compatible to the xCELLingence RATC system (ACEA, bioscience, Inc.), until they reached confluence. Freshly isolated PBMCs and 100 μl antibody-containing supernatant was added in triplicate wells per setting. Non-transgenic Huh7 cells served as specificity control. PBMCs co-cultured with Huh7S cells without antibody served as negative control. Cell viability of target cells was monitored for 120 h in real time, using the xCELLingence RATC system.

To determine the capacity of trispecific constructs to activate CTL from chronic hepatitis B patients, we isolated PBMC from a chronic carrier and used these for the experiments.

Example 2

Activation of CTL by Penta- and Octavalent Trispecific Antibody Constructs Directed Against HBsAg In a first line of experiments we have evaluated the activity of penta- and octavalent trispecific antibody constructs directed against CTL surface antigens CD3 and CD28 and the small surface antigen of HBV. We coated recombinant HBsAg to the plastic surface of cell culture dishes. To these coated wells, we added immune effector cells, namely PBMC isolated from healthy donors, and bispecific as well as trispecific antibody constructs. As negative controls we cultured the PBMC on HBsAg coated wells in the absence of bi- or trispecific antibody constructs to evaluate unspecific immune cell activation.

Figure 1:
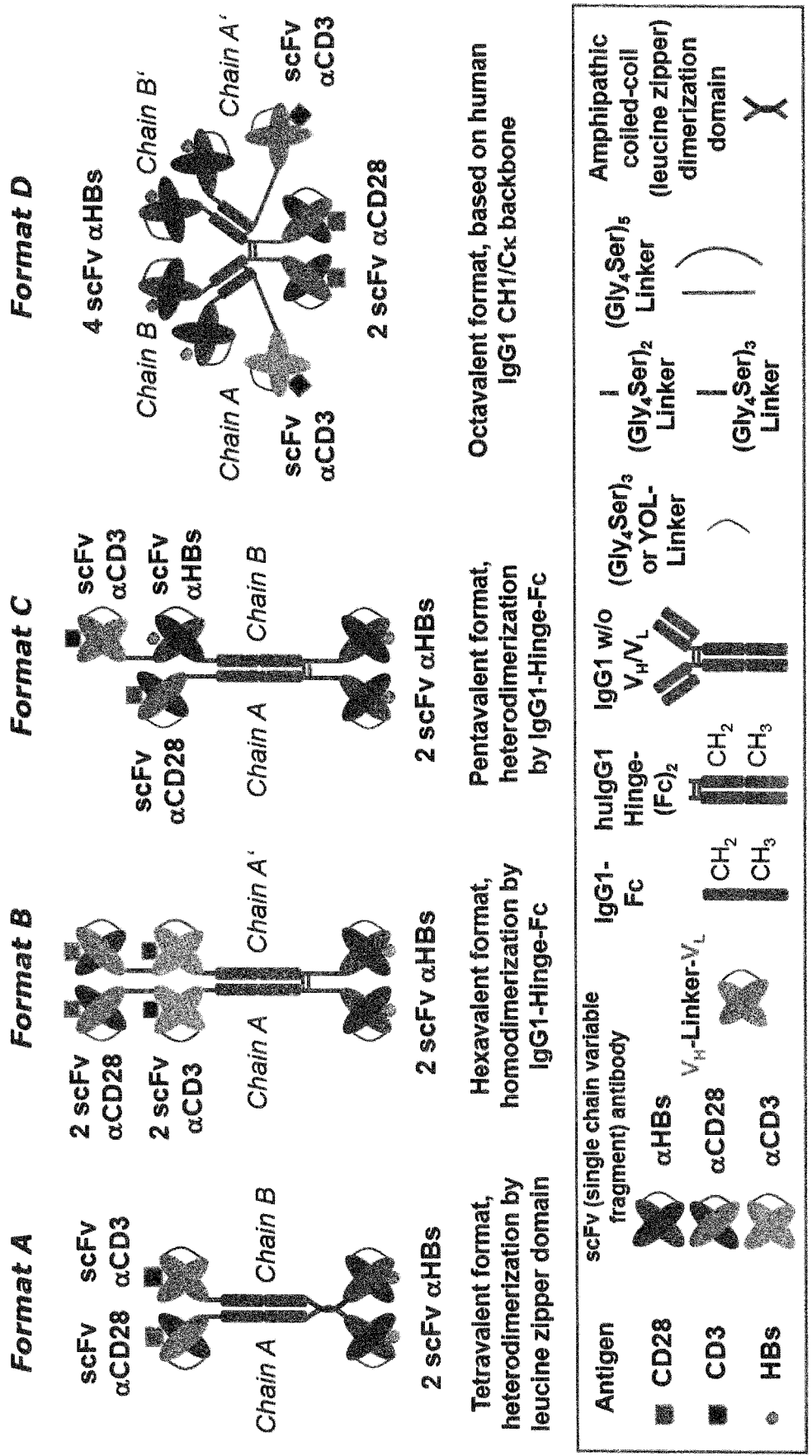
FIGS. 1 and 2 illustrate preferred trispecific binding molecules of the invention.
Figure 2:
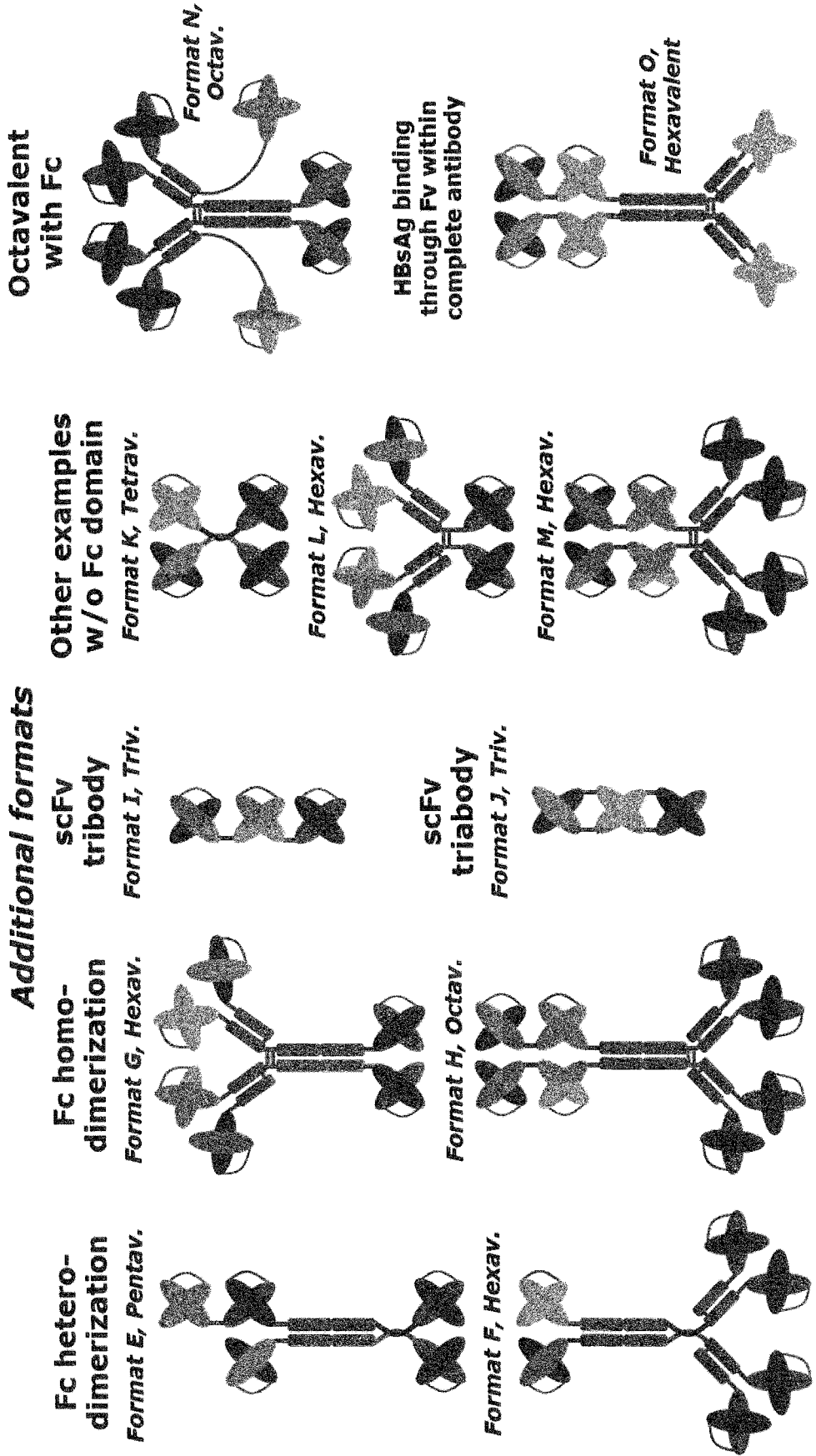
Figure 3:
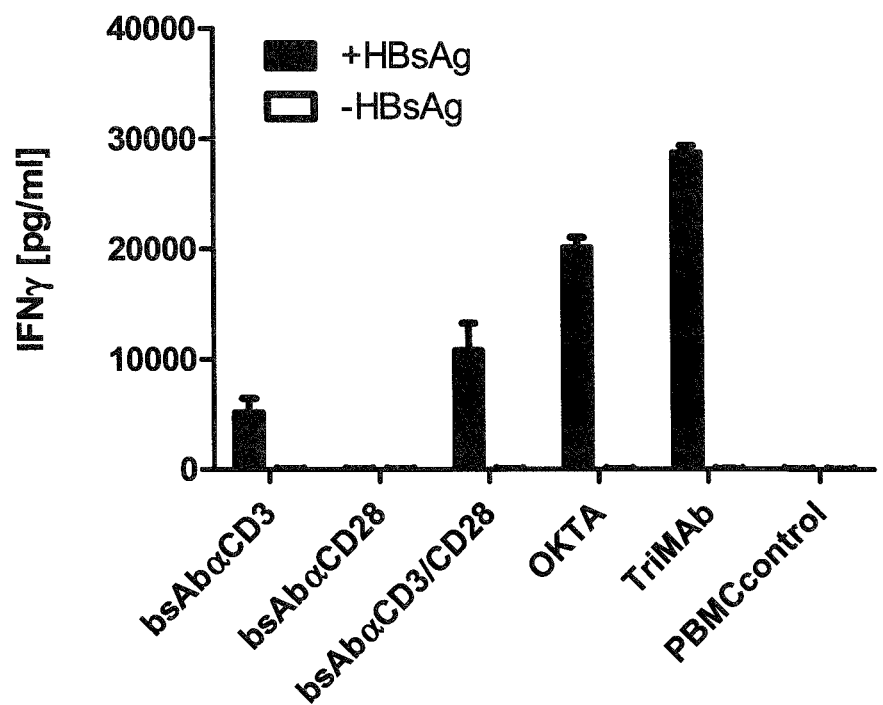
FIG. 3: T cells are activated by pentavalent and octavalent trispecific antibodies. IFNγ-secretion by T cells cultivated for 48 h on immobilized HBsAg in the presence of bi- and trispecific antibodies was determined. Combinatory application of CD3-(bsAbαCD3) and CD28-activating bispecific antibodies (bsAbαCD28) led to an enhanced secretion of IFNγ in the presence of antigen when compared to mono-treatment with CD3-activating bispecific antibodies. Application of the pentavalent (TriMAB) and octavalent (OKTA) trispecific antibody constructs induced a significantly higher secretion of interferon, with TriMAb being the most potent construct. Single treatment with CD28-activating antibodies as well as untreated control PBMCs did not show elevated levels of FNγ.

These experiments showed a specific activation of cytotoxic T lymphocytes (CTLs) upon co-culture in the presence of the CD3-activating bispecific constructs as determined by the secretion of the proinflammatory cytokine interferon gamma (IFN ☐) of up to 5000 pg/ml (FIG. 3). This effect was further enhanced upon co-administration of CD3- and CD28-specific constructs demonstrating a synergistic effect while the CD28-activating construct on its own was not able to activate T cells.

Unexpectedly, combining CD3 and CD28 stimulatory and costimulatory domains into trispecific molecules showed a significantly stronger activation of CTL than the combination of two bispecific constructs (FIG. 3) as determined by IFN ☐ secretion. This was confirmed when the cytotoxic potential of immune cells was analyzed by flow cytometry after staining for LAMP-1 translocation indicating cytotoxic vesicle degranulation and expression of granzyme B in the vast majority of cells activated by trispecific antibody constructs (FIGS. 4 A and B).

Figure 4:
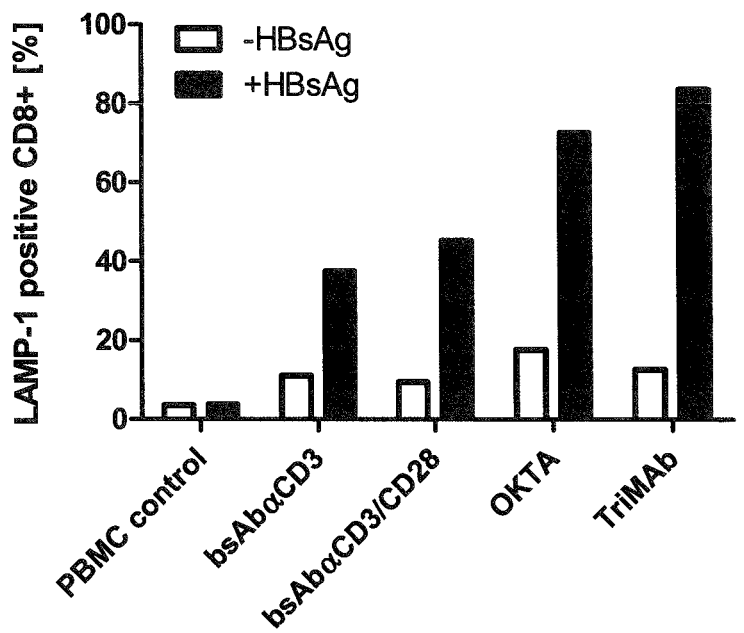
FIG. 4: T cells are activated by pentavalent and octavalent trispecific antibodies to become cytotoxic. (A) LAMP-1 translocation indicating cytotoxic activation of T cells cultivated for 48 h on immobilized HBsAg in the presence of bi- and trispecific antibodies was determined. Combinatory application of CD3-(bsAbαCD3) and CD28-activating bispecific antibodies (bsAbαCD28) led to an enhanced translocation of the degranulation marker LAMP-1 in the presence of antigen when compared to mono-treatment with CD3-activating bispecific antibodies. Application of the pentavalent (TriMAB) and octavalent (OKTA) trispecific antibody constructs induced a significantly higher levels of cytotoxic activation, with TriMAb being the most potent construct inducing degranulation in 83% of CD8+ T cells. Single treatment with CD28-activating antibodies as well as untreated control PBMCs did not show translocation of LAMP-1.
Figure 4:
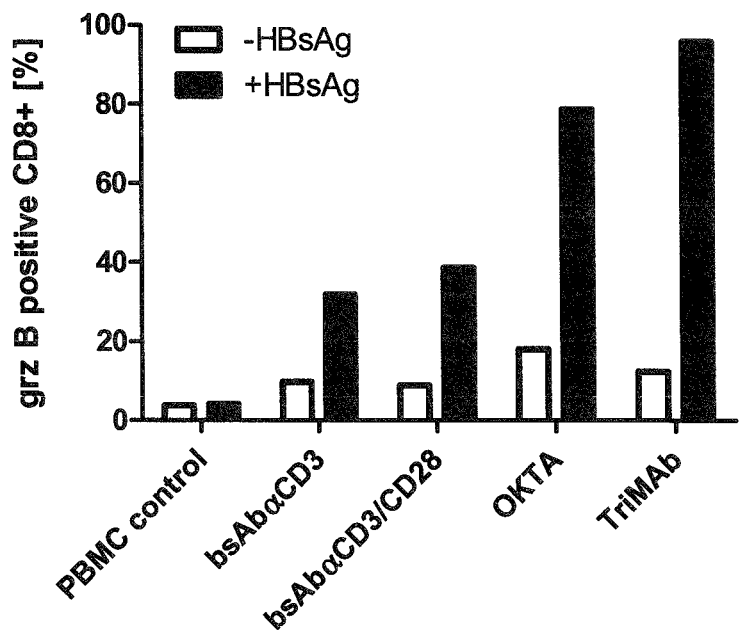

Hereby, the pentavalent construct proved most effective and was able to induce cytotoxic function in 80-95% of immune cells (FIG. 4). Since PBMC contain around 70% T cells but most of them are naïve, activation of CTL requires a strong activation of the TCR complex.

Example 3

Specific Killing of HBsAg Positive Hepatocytes upon Activation of CTL by Trispecific Antibody Constructs In a second set of experiments we have evaluated the capacity of the trispecific antibody constructs directed against CTL surface antigens CD3 and CD28 and the small surface antigen of HBV to specifically kill HBsAg expressing cells. Stably transfected Huh7 hepatoma cell lines producing HBV surface antigen (Huh7S cells) were employed as target cells. After establishing the HBV protein expression, these target cells were co-cultured together with immune effector cells, namely PBMC isolated from healthy donors, and the pentavalent trispecific antibody construct. As negative controls we analyzed co-cultures with HBV-negative target cells, which had been preincubated with HBsAg-containing supernatants. This control was employed to rule out activation of effector cells due to unspecific binding of HBV particles on the surface of HBV-negative target cells. Furthermore, HBV-positive target cells were co-cultured with immune effector cells in the absence of trispecific antibody constructs to evaluate unspecific background cytotoxicity.

These experiments showed a specific activation of CTLs upon co-culture with HuH7S cells but not with Huh7 cells in the presence of the CD3- and CD-28 activating pentavalent trispecific construct. CTL activation was determined by the secretion of the proinflammatory cytokine interferon gamma (IFN- ☐) of up to 2 ng/ml. In the absence of trispecific molecules, no CTL activation was observed (FIG. 5).

Furthermore, the trispecific construct mediated a specific cytotoxic elimination of HBsAg-producing HuH7 hepatoma cell lines (FIG. 6) as demonstrated by >90% reduction of Huh7S target cell viability in comparison to HuH7 cells or controls incubated without the addition of antibody constructs.

To further prove HBsAg specificity of CTL activation a competition assay with human serum containing neutralizing anti-HBs antibodies was performed (FIG. 7). The experiment displayed only partial competition of CTL activation as well as target cell killing when 117.5 IU/L anti-HBs were added, while the killing effect was completely abolished at a concentration of 235 IU/L anti-HBs.

Example 4

Redirection and Activation of T Cells from Chronic Hepatitis B Patients

To analyse the capacity of trispecific antibody constructs to activate CTL function in chronic hepatitis B patients, PBMC were isolated from a patient who was a high viremic hepatitis B virus carrier. Stably transfected Huh7 hepatoma cell lines producing HBV surface antigen (Huh7S cells) were employed as target cells. These target cells were co-cultured together with the PBMC isolated from the hepatitis B patient in the presence and absence of the pentavalent trispecific antibody construct. As negative controls co-cultures with HBV-negative target cells were analyzed.

These experiments showed a specific killing of HuH7S cells but not of Huh7 cells by CTL activated in PBMC of the chronic hepatitis B patient by the CD3- and CD-28 activating pentavalent trispecific construct (FIG. 8). In the absence of the trispecific antibody construct, no killing was observed demonstrating specificity of the approach and a lack of spontaneous CTL activity in PBMC of the patient. Specific CTL activation was confirmed by the secretion of the proinflammatory cytokine interferon gamma (IFN- ǀ) (FIG. 9).

The invention claimed is:

1. A binding molecule comprising three binding specificities, the binding molecule comprising:

(a) a first binding specificity for a Hepatitis B virus (HBV) surface antigen selected from HBV small surface antigen, HBV medium surface antigen and HBV large surface antigen, the first binding specificity comprising three binding sites;

(b) a second binding specificity for CD3 and (c) a third binding specificity for CD28, wherein the second and third binding specificity comprises one binding site and each of the binding sites of the first, second and third binding specificities comprises a set of six complementarity determining regions (CDRs), where said set of six CDRs consists of a first set of three CDRs and a second set of three CDRs, wherein said first and said second set is each comprised in an immunoglobulin domain.

2. The binding molecule of claim 1, comprising four binding specificities, wherein the fourth binding specificity is for hepatic cells.

3. The binding molecule of claim 1, wherein said molecule is
   (a) a multimer of polypeptides; or
   (b) a single polypeptide.

4. The binding molecule of claim 3, wherein:
   (a) each polypeptide of the multimer of polypeptides is a bispecific polypeptide; or
   (b) each polypeptide of the multimer of polypeptides is independently selected from monospecific, bispecific and trispecific polypeptides.

5. The binding molecule of claim 3, wherein the single polypeptide or one, more or all of the multimer of polypeptides comprise one or more scFv molecules.

6. The binding molecule of claim 3, wherein one, more or all binding sites is/are provided by two of said multimer of polypeptides.

7. The binding molecule of claim 6, wherein said binding molecule comprises an Fv fragment; an Fab fragment; a diabody; a triabody; a tetrabody; or an immunoglobulin G molecule, optionally with a modified Fc portion.

8. The binding molecule of claim 1, wherein the first binding specificity is for HBV small surface antigen.

9. The binding molecule of claim 1, comprising:
   A) a first and a second polypeptide, wherein
      (a) the first polypeptide consists of a structure $NH_2$-(i)-(ii)-(iii)-COOH, wherein $NH_2$ is an N-terminus of the first polypeptide and COOH is a C-terminus of the first polypeptide, (i) consists of a first single chain Fv (scFv) comprising a first binding site having the binding specificity of (a), (ii) consists of a first hinge region, $CH_2$ domain and $CH_3$ domain of a human IgG1 antibody, and (iii) consists of a second scFv comprising a second binding site having the binding specificity of (c); and
      (b) the second polypeptide consists of a structure $NH_2$-(i)-(ii)-(iii)-(iv)-COOH, wherein $NH_2$ is an N-terminus of the second polypeptide and COOH is a C-terminus of the second polypeptide, (i) consists of a third scFv comprising a third binding site having the binding specificity of (a), (ii) consists of a second hinge region, $CH_2$ domain and $CH_3$ domain of a human IgG1 antibody, (iii) consists of a fourth scFv comprising a fourth binding site having the binding specificity of (a), and (iv) consists of a fifth scFv comprising a fifth binding site having the binding specificity of (b);
      wherein the first hinge region of the first polypeptide and the second hinge region of the second polypeptide are covalently connected by two disulfide bonds, or,
   B) a first and a second polypeptide, wherein
      (a) the first polypeptide consists of the structure $NH_2$-(i)-(ii)-(iii)-COOH, wherein $NH_2$ is an N-terminus of the first polypeptide and COOH is a C-terminus of the first polypeptide, (i) consists of a first single chain Fv (scFv) comprising a first binding site having the binding specificity of (a), (ii) comprises a heavy chain variable domain and $CH_1$ domain of a human IgG1 antibody, and (iii) consists of a second scFV comprising a second binding site having the binding specificity of (c); and
      (b) the second polypeptide consists of the structure $NH_2$-(i)-(ii)-(iii)-COOH, wherein $NH_2$ is an N-terminus of the second polypeptide and COOH is a C-terminus of the second polypeptide, (i) consists of a third scFv comprising a third binding site having the binding specificity of (a), (ii) comprises a light chain variable domain and $C_L$ domain of a human $IgG_1$ antibody, and (iii) consists of a fourth scFv comprising a fourth binding site having the binding specificity of (b);
      wherein the $CH_1$ domain of the first polypeptide and the $C_L$ domain of the second polypeptide are covalently connected by a single disulfide bond, and the heavy chain variable domain of the first polypeptide and the light chain variable domain of the second polypeptide together form a fifth binding site having the binding specificity of (a).

10. The binding molecule of claim 4, wherein each polypeptide of the multimer of polypeptides is a trispecific binding molecule.

11. A pharmaceutical composition comprising or consisting of one or more binding molecules as defined in claim 1 wherein said one or more binding molecules are the only pharmaceutically active agent(s) comprised in said pharmaceutical composition.

12. A method of treating HBV infection in a subject comprising administering the binding molecule of claim 1 to the subject.

13. The binding molecule of claim 1, wherein the first binding specificity is provided by two binding sites.

14. The binding molecule of claim 1, wherein the first binding specificity is provided by three binding sites.

15. A binding molecule consisting essentially of three binding specificities, the binding molecule comprising:
   (a) a first binding specificity for a Hepatitis B virus (HBV) surface antigen selected from HBV small surface antigen, HBV medium surface antigen and HBV large surface antigen, wherein the first binding specificity comprises three binding sites;
   (b) a second binding specificity for CD3, and
   (c) a third binding specificity for CD28,
   wherein the second and third binding specificity comprises one binding site, and each of the binding sites of the first, second and third binding specificities comprises a set of six complementarity determining regions (CDRs), wherein said set of six CDRs consists of a first set of three CDRs and a second set of three CDRs, wherein said first and said second set is each comprised in an immunoglobulin domain.

* * * * *